(12) United States Patent
Moniz et al.

(10) Patent No.: US 8,536,345 B2
(45) Date of Patent: Sep. 17, 2013

(54) PROCESS FOR MAKING SUBSTITUTED 2-AMINO-THIAZOLONES

(75) Inventors: George A. Moniz, Cambridge, MA (US); Matthew J. Frizzle, Burlington (CA); Charles Bernard, Moorpark, CA (US); Michael Martinelli, San Diego, CA (US); Margaret Faul, Newbury Park, CA (US); Jay Larrow, Wakefield, MA (US); Karl B. Hansen, Cohasset, MA (US); Liane Klingensmith, Stoughton, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/999,961

(22) PCT Filed: Jun. 16, 2009

(86) PCT No.: PCT/US2009/047469
§ 371 (c)(1),
(2), (4) Date: Mar. 18, 2011

(87) PCT Pub. No.: WO2010/008729
PCT Pub. Date: Jan. 21, 2010

(65) Prior Publication Data
US 2011/0160463 A1 Jun. 30, 2011

Related U.S. Application Data

(60) Provisional application No. 61/074,345, filed on Jun. 20, 2008.

(51) Int. Cl.
*C07D 277/54* (2006.01)

(52) U.S. Cl.
USPC ....................................................... 548/184

(58) Field of Classification Search
USPC ....................................................... 548/184
See application file for complete search history.

(56) References Cited

U.S. PATENT DOCUMENTS

2010/0280255 A1* 11/2010 Moniz et al. ................. 548/184

FOREIGN PATENT DOCUMENTS

WO WO 2007/061661 A2 5/2007
WO WO 2009/002445 A1 12/2008

OTHER PUBLICATIONS

Najer et al., CA 55:144094 (1961).*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
The Search Report received in the parent International Application No. PCT/US2009/047469, dated Mar. 24, 2010.
The Office Communication received in the related European Patent Application No.: EP 09744502.7, dated Nov. 11, 2011.

* cited by examiner

*Primary Examiner* — Laura L. Stockton
(74) *Attorney, Agent, or Firm* — Foley & Lardner LLP

(57) ABSTRACT

The present invention relates to methods of making compounds that inhibit 11-β-hydroxysteroid dehydrogenase type 1 enzyme (11-β HSD1). One method comprises (a) contacting a compound of formula (II) with a chiral base, deprotonating agent, and an alkylating agent $R^3$-LG, (b) contacting the product of (a) with an acid to form a salt, and (c) reacting the salt with a base to form the compound of formula (I); wherein Z, $R^1$, $R^2$, and $R^3$ are defined herein.

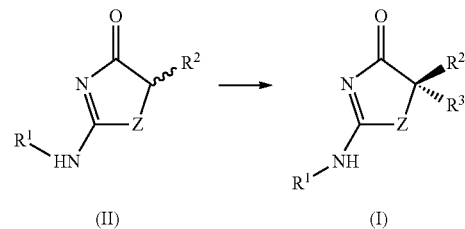

12 Claims, No Drawings

PROCESS FOR MAKING SUBSTITUTED 2-AMINO-THIAZOLONES

BACKGROUND OF THE INVENTION

The present invention relates to processes of making compounds that inhibit 11-β-hydroxysteroid dehydrogenase type 1 enzyme (11-β HSD1).

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268:4113-4125.

There exist numerous classes of HSDs. The 11-beta-hydroxysteroid dehydrogenases (11.beta.-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11.beta.-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

The various isozymes of the 17-beta-hydroxysteroid dehydrogenases (17.beta.-HSDs) bind to androgen receptors or estrogen receptors and catalyze the interconversion of various sex hormones including estradiol/estrone and testosterone/androstenedione. To date, six isozymes have been identified in humans and are expressed in various human tissues including endometrial tissue, breast tissue, colon tissue, and in the testes. 17-beta-Hydroxysteroid dehydrogenase type 2 (17.beta.-HSD2) is expressed in human endometrium and its activity has been reported to be linked to cervical cancer. Kitawaki et al., J. Clin. Endocrin. Metab., 2000, 85:1371-3292-3296. 17-beta-Hydroxysteroid dehydrogenase type 3 (17.beta.-HSD3) is expressed in the testes and its modulation may be useful for the treatment of androgen-related disorders.

Androgens and estrogens are active in their 17.beta.-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17.beta.-HSD family. 17.beta.-HSD1 catalyzes the formation of estradiol in breast tissue, which is important for the growth of malignant breast tumors. Labrie et al., Mol. Cell. Endocrinol. 1991, 78:C113-C118. A similar role has been suggested for 17.beta.-HSD4 in colon cancer. English et al., J. Clin. Endocrinol. Metab. 1999, 84:2080-2085. 17.beta.-HSD3 is almost exclusively expressed in the testes and converts androstenedione into testosterone. Deficiency of this enzyme during fetal development leads to male pseudohermaphroditism. Geissler et al., Nat. Genet. 1994, 7:34-39. Both 17.beta.-HSD3 and various 3.alpha.-HSD isozymes are involved in complex metabolic pathways which lead to androgen shuffles between inactive and active forms. Penning et al., Biochem. J. 2000, 351:67-77. Thus, modulation of certain HSDs can have potentially beneficial effects in the treatment of androgen- and estrogen-related disorders.

The 20-alpha-hydroxysteroid dehydrogenases (20.alpha.-HSDs) catalyze the interconversion of progestins (such as between progesterone and 20.alpha.-hydroxy progesterone). Other substrates for 20.alpha.-HSDs include 17.alpha.-hydroxypregnenolone or 17.alpha.-hydroxyprogesterone, leading to 20.alpha.-OH steroids. Several 20.alpha.-HSD isoforms have been identified and 20.alpha.-HSDs are expressed in various tissues, including the placenta, ovaries, testes and adrenals. Peltoketo, et al., J. Mol. Endocrinol. 1999, 23:1-11.

The 3-alpha-hydroxysteroid dehydrogenases (3.alpha.-HSDs) catalyze the interconversion of the androgens dihydrotestosterone (DHT) and 5.alpha.-androstane-3.alpha., 17.beta.-diol and the interconversion of the androgens DHEA and androstenedione and therefore play an important role in androgen metabolism. Ge et al., Biology of Reproduction 1999, 60:855-860.

1. Glucocorticoids, Diabetes and Hepatic Glucose Production

It has been known for more than half a century that glucocorticoids have a central role in diabetes. For example, the removal of the pituitary gland or the adrenal gland from a diabetic animal alleviates the most severe symptoms of diabetes and lowers the concentration of glucose in the blood (Long, C. D. and Leukins, F. D. W. (1936) J. Exp. Med. 63: 465-490; Houssay, B. A. (1942) Endocrinology 30: 884-892). It is also well established that glucocorticoids enable the effect of glucagon on the liver.

The role of 11.beta.HSD1 as an important regulator of local glucocorticoid effect and thus of hepatic glucose production is well substantiated (see, e.g., Jamieson et al. (2000) J. Endocrinol. 165: 685-692). Hepatic insulin sensitivity was improved in healthy human volunteers treated with the non-specific 11.beta.HSD1 inhibitor carbenoxolone (Walker, B. R. et al. (1995) J. Clin. Endocrinol. Metab. 80: 3155-3159). Furthermore, the expected mechanism has been established by different experiments with mice and rats. These studies showed that the mRNA levels and activities of two key enzymes in hepatic glucose production were reduced, namely: the rate-limiting enzyme in gluconeogenesis, phosphoenolpyruvate carboxykinase (PEPCK), and glucose-6-phosphatase (G6 Pase) the enzyme catalyzing the last common step of gluconeogenesis and glycogenolysis. Finally, blood glucose levels and hepatic glucose production are reduced in mice in which the 11.beta.HSD1 gene is knocked-out. Data from this model also confirm that inhibition of 11.beta.HSD1 will not cause hypoglycemia, as predicted since the basal levels of PEPCK and G6 Pase are regulated independently of glucocorticoids (Kotelevtsev, Y. et al., (1997) Proc. Natl. Acad. Sci. USA 94: 14924-14929).

FR 2,384,498 discloses compounds having a high hypoglycemic effect. Therefore, treatment of hyperglycemia with these compounds may lead to hypoglycemia.

2. Possible Reduction of Obesity and Obesity Related Cardiovascular Risk Factors Obesity is an important factor in syndrome X as well as in the majority (>80%) of type 2 diabetes, and omental fat appears to be of central importance. Abdominal obesity is closely associated with glucose intolerance, hyperinsulinemia, hypertriglyceridemia, and other factors of the so-called syndrome X (e.g. increased blood pressure, decreased levels of HDL and increased levels of VLDL) (Montague & O'Rahilly, Diabetes 49: 883-888, 2000). Inhibition of the 11.beta.HSD1 enzyme in pre-adipocytes (stromal cells) has been shown to decrease the rate of differentiation into adipocytes. This is predicted to result in diminished expansion (possibly reduction) of the omental fat depot, i.e., reduced central obesity (Bujalska, I. J., S. Kumar, and P. M. Stewart (1997) Lancet 349: 1210-1213).

Inhibition of 11.beta.HSD1 in mature adipocytes is expected to attenuate secretion of the plasminogen activator inhibitor 1 (PAI-1)—an independent cardiovascular risk factor (Halleux, C. M. et al. (1999) J. Clin. Endocrinol. Metab. 84: 4097-4105). Furthermore, there is a clear correlation between glucocorticoid "activity" and cardiovascular risk factor suggesting that a reduction of the glucocorticoid effects would be beneficial (Walker, B. R. et al. (1998) Hypertension 31: 891-895; Fraser, R. et al. (1999) Hypertension 33: 1364-1368).

Adrenalectomy attenuates the effect of fasting to increase both food intake and hypothalamic neuropeptide Y expression. This supports the role of glucocorticoids in promoting food intake and suggests that inhibition of 11.beta.HSD1 in the brain might increase satiety and therefore reduce food intake (Woods, S. C. et al. (1998) Science, 280: 1378-1383).

3. Possible Beneficial Effect on the Pancreas

Inhibition of 11.beta.HSD1 in isolated murine pancreatic .beta.-cells improves glucose-stimulated insulin secretion (Davani, B. et al. (2000) J. Biol. Chem. 2000 Nov. 10; 275 (45): 34841-4). Glucocorticoids were previously known to reduce pancreatic insulin release in vivo (Billaudel, B. and B. C. J. Sutter (1979) Horm. Metab. Res. 11: 555-560). Thus, inhibition of 11.beta.HSD1 is predicted to yield other beneficial effects for diabetes treatment, besides the effects on liver and fat.

4. Possible Beneficial Effects on Cognition and Dementia

Stress and glucocorticoids influence cognitive function (de Quervain, D. J. F., B. Roozendaal, and J. L. McGaugh (1998) Nature 394: 787-790). The enzyme 11.beta.HSD1 controls the level of glucocorticoid action in the brain and thus contributes to neurotoxicity (Rajan, V., C. R. W. Edwards, and J. R. Seckl, J. (1996) Neuroscience 16: 65-70; Seckl, J. R., Front. (2000) Neuroendocrinol. 18: 49-99). Unpublished results indicate significant memory improvement in rats treated with a non-specific 11.beta.HSD1 inhibitor (J. Seckl, personal communication). Based the above and on the known effects of glucocorticoids in the brain, it may also be suggested that inhibiting 11.beta.HSD1 in the brain may result in reduced anxiety (Tronche, F. et al. (1999) Nature Genetics 23: 99-103). Thus, taken together, the hypothesis is that inhibition of 11.beta.HSD1 in the human brain would prevent reactivation of cortisone into cortisol and protect against deleterious glucocorticoid-mediated effects on neuronal survival and other aspects of neuronal function, including cognitive impairment, depression, and increased appetite.

5. Possible Use of Immuno-Modulation Using 11.beta.HSD1 Inhibitors

The general perception is that glucocorticoids suppress the immune system. But in fact there is a dynamic interaction between the immune system and the HPA (hypothalamo-pituitary-adrenal) axis (Rook, G. A. W. (1999) Baillier's Clin. Endocrinol. Metab. 13: 576-581). The balance between the cell-mediated response and humoral responses is modulated by glucocorticoids. A high glucocorticoid activity, such as at a state of stress, is associated with a humoral response. Thus, inhibition of the enzyme 11.beta.HSD1 has been suggested as a means of shifting the response towards a cell-based reaction.

In certain disease states, including tuberculosis, lepra and psoriasis the immune reaction is normally biased towards a humoral response when in fact the appropriate response would be cell based. Temporal inhibition of 11.beta.HSD1, local or systemic, might be used to push the immune system into the appropriate response (Mason, D. (1991) Immunology Today 12: 57-60; Rook et al., supra).

An analogous use of 11.beta.HSD1 inhibition, in this case temporal, would be to booster the immune response in association with immunization to ensure that a cell based response would be obtained, when desired.

6. Reduction of Intraocular Pressure

Recent data suggest that the levels of the glucocorticoid target receptors and the 11.beta.HSD enzymes determines the susceptibility to glaucoma (Stokes, J. et al. (2000) Invest. Ophthalmol. 41: 1629-1638). Further, inhibition of 11.beta.HSD1 was recently presented as a novel approach to lower the intraocular pressure (Walker E. A. et al, poster P3-698 at the Endocrine Society meeting Jun. 12-15, 1999, San Diego). Ingestion of carbenoxolone, a non-specific inhibitor of 11.beta.HSD1, was shown to reduce the intraocular pressure by 20% in normal subjects. In the eye, expression of 11.beta.HSD1 is confined to basal cells of the corneal epithelium and the non-pigmented epithelialium of the cornea (the site of aqueous production), to ciliary muscle and to the sphincter and dilator muscles of the iris. In contrast, the distant isoenzyme 11.beta.HSD2 is highly expressed in the non-pigmented ciliary epithelium and corneal endothelium. None of the enzymes is found at the trabecular meshwork, the site of drainage. Thus, 11.beta.HSD1 is suggested to have a role in aqueous production, rather than drainage, but it is presently unknown if this is by interfering with activation of the glucocorticoid or the mineralocorticoid receptor, or both.

7. Reduced Osteoporosis

Glucocorticoids have an essential role in skeletal development and function but are detrimental in excess. Glucocorticoid-induced bone loss is derived, at least in part, via inhibition of bone formation, which includes suppression of osteoblast proliferation and collagen synthesis (Kim, C. H., Cheng, S. L. and Kim, G. S. (1999) J. Endocrinol. 162: 371-379). The negative effect on bone nodule formation could be blocked by the non-specific inhibitor carbenoxolone suggesting an important role of 11.beta.HSD1 in the glucocorticoid effect (Bellows, C. G., Ciaccia, A. and Heersche, J. N. M. (1998) Bone 23: 119-125). Other data suggest a role of 11.beta.HSD1 in providing sufficiently high levels of active glucocorticoid in osteoclasts, and thus in augmenting bone resorption (Cooper, M. S. et al. (2000) Bone 27: 375-381). Taken together, these different data suggest that inhibition of 11.beta.HSD1 may have beneficial effects against osteoporosis by more than one mechanism working in parallel.

8. Reduction of Hypertension

Bile acids inhibit 11.beta.-hydroxysteroid dehydrogenase type 2. This results in a shift in the overall body balance in favour of cortisol over cortisone, as shown by studying the ratio of the urinary metabolites (Quattropani, C., Vogt, B., Odermatt, A., Dick, B., Frey, B. M., Frey, F. J. (2001) J Clin Invest. November; 108(9):1299-305. "Reduced activity of 11beta-hydroxysteroid dehydrogenase in patients with cholestasis".). Reducing the activity of 11bHSD1 in the liver by a selective inhibitor is predicted to reverse this imbalance, and acutely counter the symptoms such as hypertension, while awaiting surgical treatment removing the biliary obstruction.

WO 99/65884 discloses carbon substituted aminothiazole inhibitors of cyclin dependent kinases. These compounds may, e.g., be used against cancer, inflammation and arthritis. U.S. Pat. No. 5,856,347 discloses an antibacterial preparation or bactericide comprising 2-aminothiazole derivative and/or salt thereof. Further, U.S. Pat. No. 5,403,857 discloses benzenesulfonamide derivatives having 5-lipoxygenase inhibitory activity. Additionally, tetrahydrothiazolo[5,4-c]pyridines are disclosed in: Analgesic tetrahydrothiazolo[5,4-c]pyridines. Fr. Addn. (1969), 18 pp, Addn. to Fr. 1498465. CODEN: FAXXA3; FR 94123 19690704 CAN 72:100685 AN 1970:100685 CAPLUS and 4,5,6,7-Tetrahydrothiazolo[5,4-c]pyridines. Neth. Appl. (1967), 39 pp. CODEN: NAXXAN NL 6610324 19670124 CAN 68:49593, AN 1968:

49593 CAPLUS. However, none of the above disclosures discloses processes of making the compounds according to the present invention.

9. Wound Healing

Cortisol performs a broad range of metabolic functions and other functions. The multitude of glucocorticoid action is exemplified in patients with prolonged increase in plasma glucocorticoids, so called "Cushing's syndrome." Patients with Cushing's syndrome have prolonged increase in plasma glucocorticoids and exhibit impaired glucose tolerance, type 2 diabetes, central obesity, and osteoporosis. These patients also have impaired wound healing and brittle skin (Ganong, W. F. Review of Medical Physiology. Eighteenth edition ed. Stamford, Conn.: Appleton & Lange; 1997).

Glucocorticoids have been shown to increase risk of infection and delay healing of open wounds (Anstead, G. M. Steroids, retinoids, and wound healing. Adv Wound Care 1998; 11(6):277-85). Patients treated with glucocorticoids have 2-5-fold increased risk of complications when undergoing surgery (Diethelm, A. G. Surgical management of complications of steroid therapy. Ann Surg 1977; 185(3):251-63).

The European patent application No. EP 0902288 discloses a method for diagnosing the status of wound healing in a patient, comprising detecting cortisol levels in said wound. The authors suggest that elevated levels of cortisol in wound fluid, relative to normal plasma levels in healthy individuals, correlates with large, non-healing wounds (Hutchinson, T. C., Swaniker, H. P., Wound diagnosis by quantitating cortisol in wound fluids. European patent application No. EP 0 902 288, published 17 Mar. 1999).

In humans, the 11.beta.-HSD catalyzes the conversion of cortisol to cortisone, and vice versa. The parallel function of 11.beta.-HSD in rodents is the interconversion of corticosterone and 11-dehydrocorticosterone (Frey, F. J., Escher, G., Frey, B. M. Pharmacology of 11 beta-hydroxysteroid dehydrogenase. Steroids 1994; 59(2):74-9). Two isoenzymes of 11.beta.-HSD, 11.beta.-HSD1 and 11.beta.-HSD2, have been characterized, and differ from each other in function and tissue distribution (Albiston, A. L., Obeyesekere, V. R., Smith, R. E., Krozowski, Z. S. Cloning and tissue distribution of the human 11 beta-hydroxysteroid dehydrogenase type 2 enzyme. Mol Cell Endocrinol 1994; 105(2):R11-7). Like GR, 11.beta.-HSD1 is expressed in numerous tissues like liver, adipose tissue, adrenal cortex, gonads, lung, pituitary, brain, eye etc (Monder C, White P C. 11 beta-hydroxysteroid dehydrogenase. Vitam Horm 1993; 47:187-271; Stewart, P. M., Krozowski, Z. S. 11 beta-Hydroxysteroid dehydrogenase. Vitam Horm 1999; 57:249-324; Stokes, J., Noble, J., Brett, L., Phillips, C., Seckl, J. R., O'Brien, C., et al. Distribution of glucocorticoid and mineralocorticoid receptors and 11beta-hydroxysteroid dehydrogenases in human and rat ocular tissues. Invest Ophthalmol V is Sci 2000; 41(7):1629-38). The function of 11.beta.-HSD1 is to fine-tune local glucocorticoid action. 11.beta.-HSD activity has been shown in the skin of humans and rodents, in human fibroblasts and in rat skin pouch tissue (Hammami, M. M., Siiteri, P. K. Regulation of 11 beta-hydroxysteroid dehydrogenase activity in human skin fibroblasts: enzymatic modulation of glucocorticoid action. J Clin Endocrinol Metab 1991; 73(2):326-34); Cooper, M. S., Moore, J., Filer, A., Buckley, C. D., Hewison, M., Stewart, P. M. 11beta-hydroxysteroid dehydrogenase in human fibroblasts: expression and regulation depends on tissue of origin. ENDO 2003 Abstracts 2003; Teelucksingh, S., Mackie, A. D., Burt, D., McIntyre, M. A., Brett, L., Edwards, C. R. Potentiation of hydrocortisone activity in skin by glycyrrhetinic acid. Lancet 1990; 335(8697):1060-3; Slight, S. H., Chilakamarri, V. K., Nasr, S., Dhalla, A. K., Ramires, F. J., Sun, Y., et al. Inhibition of tissue repair by spironolactone: role of mineralocorticoids in fibrous tissue formation. Mol Cell Biochem 1998; 189(1-2):47-54).

Wound healing consists of serial events including inflammation, fibroblast proliferation, secretion of ground substances, collagen production, angiogenesis, wound contraction and epithelialization. It can be divided in three phases; inflammatory, proliferative and remodeling phase (reviewed in Anstead et al., supra).

In surgical patients, treatment with glucocorticoids increases risk of wound infection and delay healing of open wounds. It has been shown in animal models that restraint stress slows down cutaneous wound healing and increases susceptibility to bacterial infection during wound healing. These effects were reversed by treatment with the glucocorticoid receptor antagonist RU486 (Mercado, A. M., Quan, N., Padgett, D. A., Sheridan, J. F., Marucha, P. T. Restraint stress alters the expression of interleukin-1 and keratinocyte growth factor at the wound site: an in situ hybridization study. J Neuroimmunol 2002; 129(1-2):74-83; Rojas, I. G., Padgett, D. A., Sheridan, J. F., Marucha, P. T. Stress-induced susceptibility to bacterial infection during cutaneous wound healing. Brain Behav Immun 2002; 16(1):74-84). Glucocorticoids produce these effects by suppressing inflammation, decrease wound strength, inhibit wound contracture and delay epithelialization (Anstead et al., supra). Glucocorticoids influence wound healing by interfering with production or action of cytokines and growth factors like IGF, TGF-.beta., EGF, KGF and PDGF (Beer, H. D., Fassler, R., Werner, S. Glucocorticoid-regulated gene expression during cutaneous wound repair. Vitam Horm 2000; 59:217-39; Hamon, G. A., Hunt, T. K., Spencer, E. M. In vivo effects of systemic insulin-like growth factor-I alone and complexed with insulin-like growth factor binding protein-3 on corticosteroid suppressed wounds. Growth Regul 1993; 3(1):53-6; Laato, M., Heino, J., Kahari, V. M., Niinikoski, J., Gerdin, B. Epidermal growth factor (EGF) prevents methylprednisolone-induced inhibition of wound healing. J Surg Res 1989; 47(4):354-9; Pierce, G. F., Mustoe, T. A., Lingelbach, J., Masakowski, V. R., Gramates, P., Deuel, T. F. Transforming growth factor beta reverses the glucocorticoid-induced wound-healing deficit in rats: possible regulation in macrophages by platelet-derived growth factor. Proc Natl Acad Sci USA 1989; 86(7):2229-33). It has also been shown that glucocorticoids decrease collagen synthesis in rat and mouse skin in vivo and in rat and human fibroblasts (Oishi, Y., Fu, Z. W., Ohnuki, Y., Kato, H., Noguchi, T. Molecular basis of the alteration in skin collagen metabolism in response to in vivo dexamethasone treatment: effects on the synthesis of collagen type I and III, collagenase, and tissue inhibitors of metalloproteinases. Br J Dermatol 2002; 147(5):859-68).

U.S. Patent Application Publication No. 2006/0142357 and WO 2005/116002 describe 11-β-HSD1 inhibitors of the following general structure and certain processes for making the same:

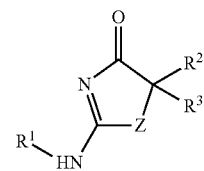

It is evident that this type of 11-β-HSD1 inhibitors is of great importance from a medicinal point of view. There is, therefore, a need for an efficient process to synthesize these compounds, particularly the optical isomers thereof in high purity, for large scale preparation suitable for commercial production.

SUMMARY OF THE INVENTION

The present invention provides in one embodiment a process for the preparation of compounds having formula I, or a tautomer, stereoisomer, geometric isomer, optical isomer, hydrate, solvate, prodrug, or pharmaceutically acceptable salt thereof:

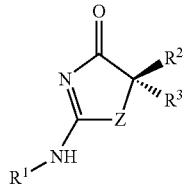

(I)

Variable Z is S or O.

$R^1$ is selected from $C_{1-8}$ alkyl, $C_{2-8}$ alkenyl, $C_{3-10}$-cycloalkyl, $C_{3-10}$-cycloalkenyl, $C_{3-10}$-cycloalkenyl-$C_{1-8}$-alkyl, aryl, aryl-$C_{1-8}$-alkyl, heterocyclyl, heterocyclyl-$C_{1-4}$-alkyl and haloalkyl. In the definition of $R^1$, any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^4R^5N$—$C_1$-$C_8$-alkyl, $C_1$-$C_8$-alkyl-$OR^6$, —$OR^6$, ($C_3$-$C_{10}$)-cycloalkyl or $C_1$-$C_8$-alkyl-sulfonyl.

$R^2$ and $R^3$ are independently selected from $C_{1-8}$-alkyl, $C_{1-4}$-alkoxy, $C_{3-10}$-cycloalkyl, heterocyclyl, $C_{3-10}$-cycloalkyl-$C_{1-8}$-alkyl, CN—$C_{1-8}$-alkyl, aryl, aryl-$C_{1-8}$-alkyl, heterocyclyl-$C_{1-8}$-alkyl and haloalkyl. In the definitions for $R^2$ and $R^3$, any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^4R^5N$—$C_1$-$C_8$-alkyl, $C_1$-$C_8$-alkyl-$OR^6$, —$OR^6$, ($C_3$-$C_{10}$)-cycloalkyl or $C_1$-$C_8$-alkyl-sulfonyl.

$R^4$ and $R^5$ are each independently selected from hydrogen, $C_1$-$C_8$ alkyl, $C_1$-$C_8$ alkoxy, —$NR^6R^6$, —S—($C_1$-$C_8$)alkyl, aryl and heterocyclyl. In the definitions for $R^4$ and $R^5$, any alkyl, alkoxy, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl.

$R^6$ is independently selected from hydrogen, $C_1$-$C_8$ alkyl, aryl-$C_1$-$C_8$ alkyl, $C_1$-$C_8$ alkoxy, —S—($C_1$-$C_8$)alkyl, heterocyclyl and aryl. In the definition for $R^6$, any alkyl, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl.

The process comprises the following steps:

(a) contacting a compound of formula II with (i) a chiral base in the presence of an amine, and an alkylating agent $R_3$-LG; wherein LG is a leaving group;

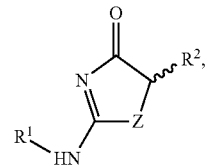

(II)

(b) contacting the product of (a) with an acid HB to form a salt of formula I' wherein B is an organic or inorganic anion; and

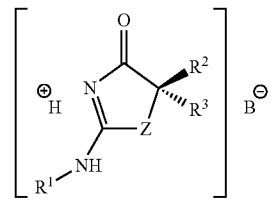

(I')

(c) reacting the salt of formula I' with a base to yield the compound of formula I.

In another embodiment, the invention provides another process for the preparation of a compound having formula I, or a tautomer, stereoisomer, geometric isomer, optical isomer, hydrate, solvate, prodrug, or pharmaceutically acceptable salt thereof:

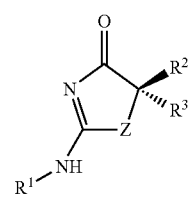

(I)

The process comprises contacting a compound of formula II

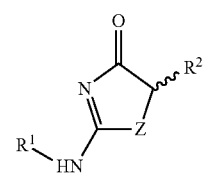

(II)

with a chiral base in the presence of a deprotonating reagent and alkylating agent $R^3$-LG. Z is S or O.

$R^1$ is selected from $C_{1-8}$ alkyl, $C_{2-8}$ alkenyl, $C_{3-10}$-cycloalkyl, $C_{3-10}$-cycloalkenyl, $C_{3-10}$-cycloalkyl-$C_{1-8}$-alkyl, $C_{3-10}$-cycloalkenyl-$C_{1-8}$-alkyl, aryl, aryl-$C_{1-8}$-alkyl, heterocyclyl, heterocyclyl-$C_{1-8}$-alkyl and haloalkyl; wherein any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^4R^5N$—$C_1$-$C_8$-alkyl, $C_1$-$C_8$-alkyl-$OR^6$, —$OR^6$, ($C_3$-$C_{10}$)-cycloalkyl or $C_1$-$C_8$-alkyl-sulfonyl.

$R^2$ and $R^3$ are independently selected from $C_{1-8}$-alkyl, $C_{1-8}$-alkoxy, $C_{3-10}$-cycloalkyl, heterocyclyl, $C_{3-10}$-cycloalkyl-$C_{1-8}$-alkyl, CN—$C_{1-8}$-alkyl, aryl, aryl-$C_{1-8}$-alkyl, heterocyclyl-$C_{1-8}$-alkyl and haloalkyl; wherein any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^4R^5N$—$C_1$-$C_8$-alkyl, $C_1$-$C_8$-alkyl-$OR^6$, —$OR^6$, $(C_3$-$C_{10})$-cycloalkyl or $C_1$-$C_8$-alkyl-sulfonyl.

$R^4$ and $R^5$ are each independently selected from hydrogen, $C_1$-$C_8$ alkyl, $C_1$-$C_8$ alkoxy, —$NR^6R^6$, —S—$(C_1$-$C_8)$alkyl, aryl and heterocyclyl; where in the definition of $R^4$ and $R^5$ any alkyl, alkoxy, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl.

$R^6$ is independently selected from hydrogen, $C_1$-$C_8$ alkyl, aryl-$C_1$-$C_8$ alkyl, $C_1$-$C_8$ alkoxy, —S—$(C_1$-$C_8)$alkyl, heterocyclyl and aryl; where in the definition of $R^6$ any alkyl, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl.

LG is a leaving group.

Another embodiment of the invention is a process for preparing a compound of formula III:

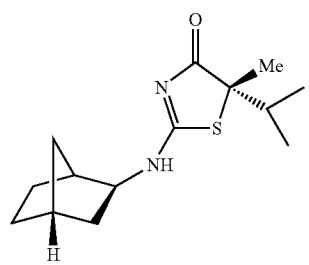
(III)

In one embodiment, the process comprises the following steps:
(a) contacting a compound of formula IV

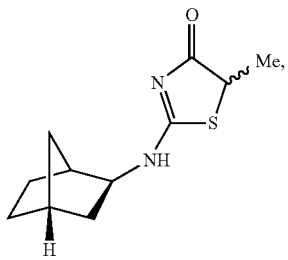
(IV)

with a chiral base of the formula

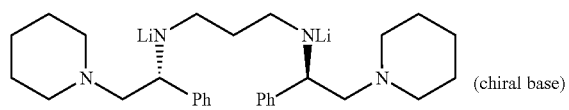
(chiral base)

in the presence of N,N,N',N'-tetramethylethylenediamine (TMEDA), and
(b) reacting the product of step (a) with isopropyl iodide.

In one embodiment, the process further comprises the following steps:
(c) contacting the product of step (b) with $MeSO_3H$ to form a mesylate salt, and
(d) reacting the mesylate salt from step (c) with NaOH to yield the compound of formula III.

In still another embodiment, the process further comprises the step of isolating the mesylate salt after step (c) and before step (d).

Another embodiment of the invention is a process for the preparation of a compound according to formula V:

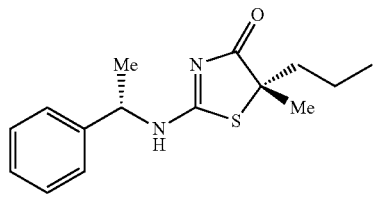
(V)

The process comprises
(a) contacting a compound of formula (VI)

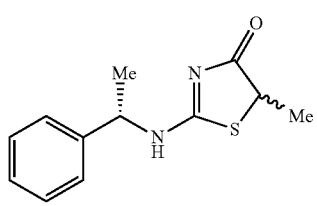
(VI)

with a chiral base of the formula

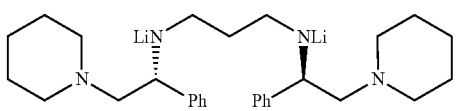

in the presence of TMEDA; and
(b) reacting the product of step (a) with n-propyl iodide.

DETAILED DESCRIPTION

The various terms used, separately and in combinations, in the processes herein described are defined below.

The expression "comprising" means "including but not limited to." Thus, other non-mentioned substances, additives, carriers, or steps may be present.

The term "aryl" in the present description is intended to include aromatic rings (monocyclic or bicyclic) having from 6 to 10 ring carbon atoms, such as phenyl (Ph), naphthyl, and indanyl (i.e., 2,3-dihydroindenyl). An aryl group may be substituted by $C_{1-6}$-alkyl. Examples of substituted aryl groups are benzyl, and 2-methylphenyl.

The term "heteroaryl" is a monocyclic, bi- or tricyclic aromatic ring system (only one ring need to be aromatic) having from 5 to 14 ring atoms (mono- or bicyclic), in which one or more of the ring atoms are other than carbon, such as nitrogen, sulfur, oxygen and selenium as part of the ring system. In some embodiments, the ring has from 5 to 10 ring atoms such as 5, 6, 7, 8, 9 or 10. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, quinoline, quinoxaline, isoquinoline, phthalazine, cinnoline, quinazoline, indole, isoindole, benzothiophene, benzofuran, isobenzofuran, benzoxazole, 2,1,3-benzoxadiazole, benzopyrazole; benzothiazole, 2,1,3-benzothiazole, 2,1,3-benzoselenadiazole, benzimidazole, indazole, benzodioxane, indane, 1,5-naphthyridine, 1,8-naphthyridine, acridine, fenazine and xanthene.

The term "heterocyclic" and "heterocyclyl" relates to unsaturated as well as partially and fully saturated mono-, bi- and tricyclic rings having from 4 to 14 ring atoms having one or more heteroatoms (e.g., oxygen, sulfur, or nitrogen) as part of the ring system and the reminder being carbon, such as, for example, the heteroaryl groups mentioned above as well as the corresponding partially saturated or fully saturated heterocyclic rings. Exemplary saturated heterocyclic rings are azetidine, pyrrolidine, piperidine, piperazine, morpholine, thiomorpholine, 1,4-oxazepane, azepane, phthalimide, indoline, isoindoline, 1,2,3,4-tetrahydroquinoline, 1,2,3,4-tetrahydroisoquinoline, 3,4-dihydro-2H-1,4-benzoxazine, hexahydroazepine, 3,4-dihydro-2(1H)isoquinoline, 2,3-dihydro-1H-indole, 1,3-dihydro-2H-isoindole, azocane, 1-oxa-4-azaspiro[4.5]dec-4-ene, decahydroisoquinoline, and 1,4-diazepane. In addition, the heterocyclyl or heterocyclic moiety may optionally be substituted with one or more oxo groups.

$C_{1-8}$-alkyl is a straight or branched alkyl group containing 1-8 carbon atoms. Exemplary alkyl groups include methyl, ethyl, n-propyl, isopropyl, n-butyl, sec-butyl, tert-butyl, pentyl, isopentyl, hexyl, isohexyl, n-heptyl, and n-octyl. For parts of the range "$C_{1-8}$-alkyl" all subgroups thereof are contemplated such as $C_{1-7}$-alkyl, $C_{1-6}$-alkyl, $C_{1-5}$-alkyl, $C_{1-4}$-alkyl, $C_{2-8}$-alkyl, $C_{2-7}$-alkyl, $C_{3-7}$-alkyl, $C_{4-6}$-alkyl, etc.

$C_{1-8}$-alkoxy is a straight or branched alkoxy group containing 1-8 carbon atoms. Exemplary alkoxy groups include methoxy, ethoxy, propoxy, isopropoxy, butoxy, sec-butoxy, tert-butoxy, pentyloxy, isopentyloxy, hexyloxy, isohexyloxy, n-heptyloxy, and n-octyloxy. For parts of the range "$C_{1-6}$-alkoxy" all subgroups thereof are contemplated such as $C_{1-7}$-alkoxy, $C_{1-6}$-alkoxy, $C_{1-5}$-alkoxy, $C_{1-4}$-alkoxy, $C_{2-8}$-alkoxy, $C_{2-7}$-alkoxy, $C_{2-6}$-alkoxy, $C_{2-5}$-alkoxy, $C_{3-7}$-alkoxy, $C_{4-6}$-alkoxy, etc.

$C_{2-8}$-alkenyl is a straight or branched alkenyl group containing 2-8 carbon atoms. Exemplary alkenyl groups include vinyl, 1-propenyl, 2-propenyl, isopropenyl, 1-butenyl, 2-butenyl, 1-pentenyl, 2-pentenyl, 1-hexenyl, 2-hexenyl, 1-heptenyl, and 1-octenyl. For parts of the range "$C_{2-8}$-alkenyl" all subgroups thereof are contemplated such as $C_{2-7}$-alkenyl, $C_{2-6}$-alkenyl, $C_{2-5}$-alkenyl, $C_{2-4}$-alkenyl, $C_{3-8}$-alkenyl, $C_{3-7}$-alkenyl, $C_{3-6}$-alkenyl, $C_{3-5}$-alkenyl, $C_{4-7}$-alkenyl, $C_{5-6}$-alkenyl, etc.

$C_{3-10}$-cycloalkyl is an optionally substituted monocyclic, bicyclic or tricyclic alkyl group containing between 3-10 carbon atoms. Exemplary cycloalkyl groups include cyclopropyl, cyclobutyl, cyclopentyl, cyclohexyl, cycloheptyl, cyclooctyl, cyclononyl, cyclodecyl, bicyclo[2.2.1]hept-2-yl, tricyclo[3.3.1.0~3,7~]non-3-yl, (1R,2R,3R,5S)-2,6,6-trimethylbicyclo[3.1.1]hept-3-yl, (1S,2S,3S,5R)-2,6,6-trimethylbicyclo[3.1.1]hept-3-yl, 1-adamantyl, noradamantyl, and 2,2,3,3-tetramethylcyclopropyl. For parts of the range "$C_{3-10}$-cycloalkyl" all subgroups thereof are contemplated such as $C_{3-9}$-cycloalkyl, $C_{3-8}$-cycloalkyl, $C_{3-7}$-cycloalkyl, $C_{3-6}$-cycloalkyl, $C_{3-5}$-cycloalkyl, $C_{4-10}$-cycloalkyl, $C_{5-10}$-cycloalkyl, $C_{6-10}$-cycloalkyl, $C_{7-10}$-cycloalkyl, $C_{8-9}$-cycloalkyl, etc. In addition, the cycloalkyl moiety can be substituted with one or more oxo groups.

$C_{3-10}$-cycloalkenyl is an optionally alkyl substituted cyclic, bicyclic or tricyclic alkenyl group containing totally 3-10 carbon atoms. Exemplary cycloalkenyl groups include cyclopropenyl, cyclobutenyl, cyclopentenyl, cyclohexenyl, cycloheptenyl, cyclooctenyl, cyclononenyl, cyclodecenyl, and bicyclo[2.2.1]hept-5-en-2-yl. For parts of the range "$C_{3-10}$-cycloalkenyl" all subgroups thereof are contemplated such as $C_{3-9}$-cycloalkenyl, $C_{3-8}$-cycloalkenyl, $C_{3-7}$-cycloalkenyl, $C_{3-6}$-cycloalkenyl, $C_{3-5}$-cycloalkenyl, $C_{4-10}$-cycloalkenyl, $C_{5-10}$-cycloalkenyl, $C_{6-10}$-cycloalkenyl, $C_{7-10}$-cycloalkenyl, $C_{8-9}$-cycloalkenyl, etc. In addition, the cycloalkenyl moiety may optionally be substituted with one or more oxo groups.

The terms "halogen" and "halo" in the present description is intended to include fluorine, chlorine, bromine and iodine.

The term "-hetero($C_1$-$C_8$)alkyl" refers to a moiety wherein a hetero atom, selected from optionally substituted nitrogen, sulfur and oxygen, is the point of attachment to the core molecule and is attached to a $C_1$-$C_8$ alkyl chain.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject for the treatment of disease, 11-.beta.-HSD1 inhibition, 11-.beta.-HSD1-mediated disease).

As used herein, the term "prodrug" means a derivative of a compound that can hydrolyze, oxidize, or otherwise react under biological conditions (in vitro or in vivo) to provide an active compound Examples of prodrugs include, but are not limited to, derivatives and metabolites of a compound derivative that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gila).

A "tautomer" is one of two or more structural isomers that exist in equilibrium and is readily converted from one isomeric form to another. In the present case, tautomers of the structures below are encompassed by the present invention.

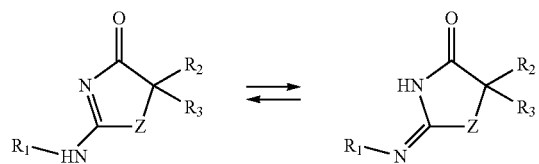

As used herein, "hydrate" is a form of a compound wherein water molecules are combined in a certain ratio as an integral part of the crystal structure of the compound.

As used herein, "solvate" is a form of a compound where solvent molecules are combined in a certain ratio as an integral part of the crystal structure of the compound.

As used herein, the term "geometrical isomers" refers compounds that have the same molecular formula but the atoms are in different non-equivalent positions relative to one another.

As used herein, the term "optical isomers" refers to compounds with chiral atoms which have the ability to rotate plane polarized light, and are typically designated using the conventional R/S configuration. The term "optical isomer" includes enantiomers and diastereomers as well as compounds which can be distinguished one from the other by the designations of (D) and (L).

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included in the invention are pharmaceutically acceptable salts or compounds of any of the formulae herein.

Depending on its structure, the phrase "pharmaceutically acceptable salt," as used herein, refers to a pharmaceutically acceptable organic or inorganic acid or base salt of a compound. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

The following abbreviations are used throughout the description and appended claims, and they have the following meanings:

"TMEDA" means N,N,N'N'-tetramethylethylenediamine.
"TMPDA" means N,N,N'N'-tetramethylpropylenediamine.
"TMBDA" means N,N,N'N'-tetramethylbutylenediamine.
"Ar" means aryl.
"Ph" means phenyl.
"de" means diastereomeric excess.
"MTBE" means methyl tertiary-butyl ether.
"IPA" means isopropyl alcohol.
"DCM" means dichloromethane.
"MSA" means methane sulfonic acid (MeSO$_3$H).
"Tint" means the internal temperature of the reaction mixture.
"LCAP" means Peak Area % by HPLC
"TGA" means Thermogravimetric Analysis The chemicals used in the synthetic routes delineated herein include, for example, solvents, reagents, and catalysts. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

Some embodiments of the present invention contemplate processes of making a compound of the general formula I, as described above, via asymmetric alkylation of a compound of formula II:

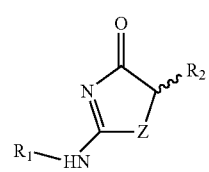

The compound of formula (II) is prepared by the following general synthetic method:

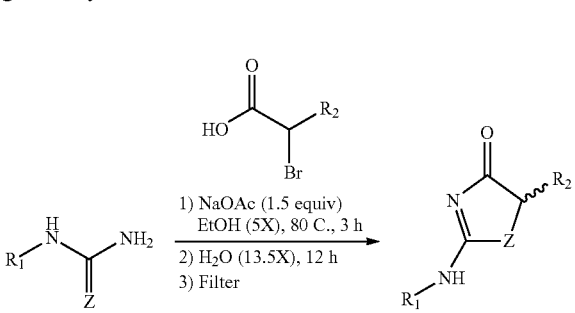

If the appropriate urea, thiourea, or alpha-bromocarboxylic acid or ester is not commercially available, the appropriate starting material can be prepared in accordance with the methods described in U.S. Patent Application Publication No. 2006/0142357.

In one embodiment, Z is S, referring to thiazolinones. Variable Z also can be O, referring to oxazolinones.

In another embodiment, $R_1$ is selected from the group consisting of

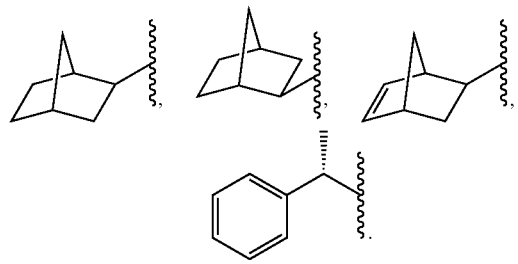

and

An exemplary value for $R^1$ is:

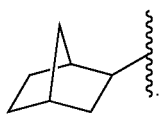

In one embodiment, $R_2$ and $R_3$ are independently selected from methyl, isopropyl, and n-propyl.

In another embodiment, the chiral base is selected from the following group of bases:

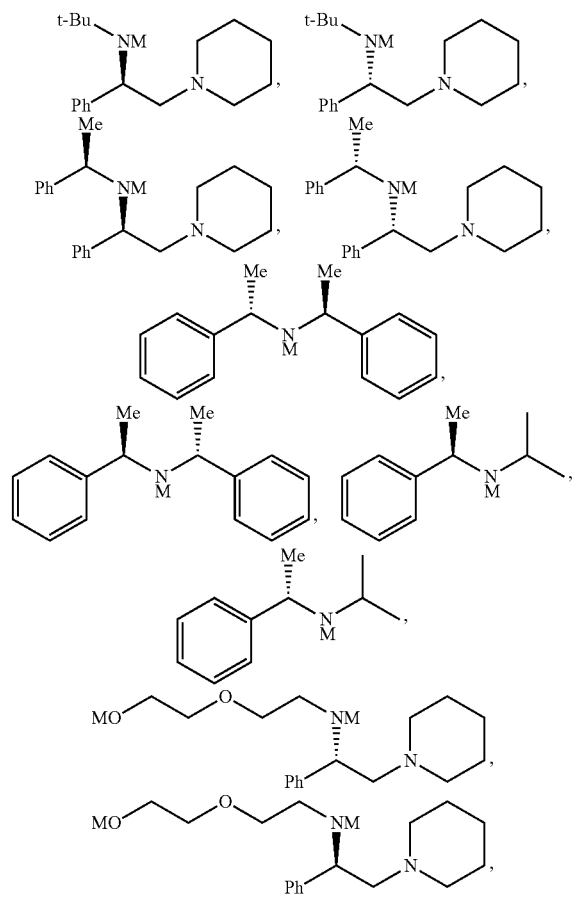

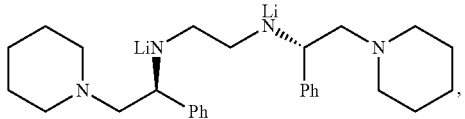

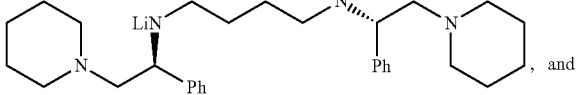

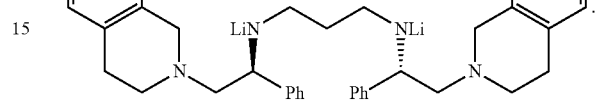

In another embodiment, the chiral base is selected from

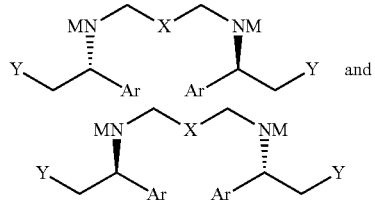

and wherein:
X is selected from O, N, S, and $C_{1-8}$-alkylene;
Y is selected from $C_{1-8}$-alkyl, aryl, and heterocyclyl; and
M is selected from Li, Na, K, Cs, Cu, Zn, and Mg; and
Ar is aryl.

In another embodiment, the chiral base is

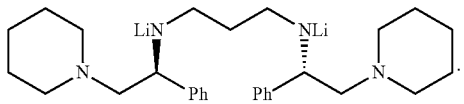

In some embodiments, the chiral base is selected from the group consisting of:

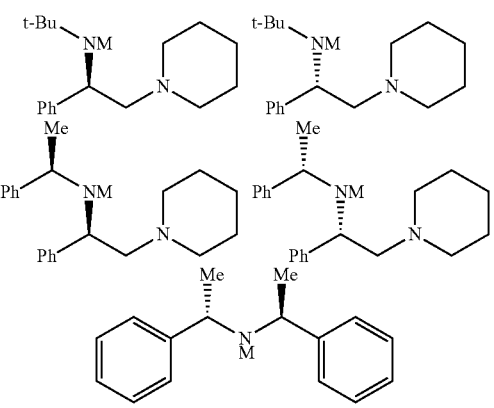

-continued

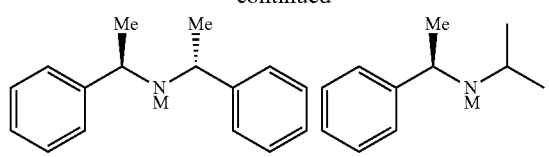

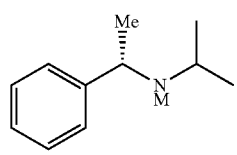

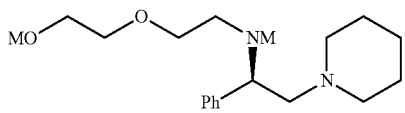

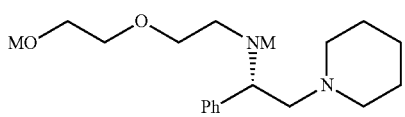

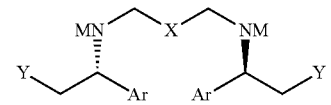

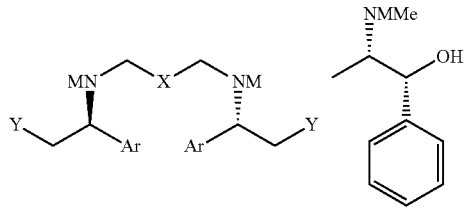

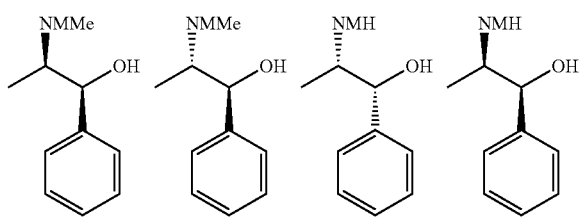

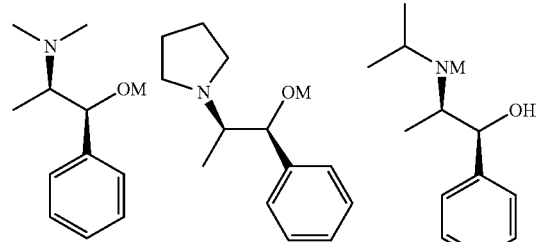

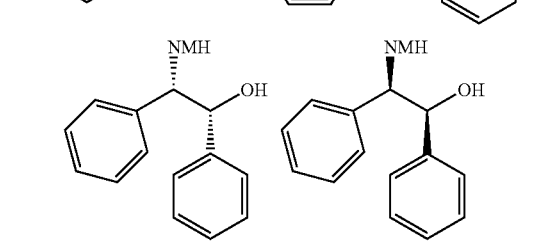

-continued

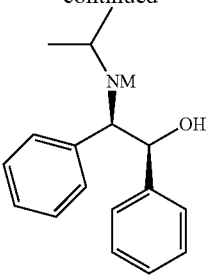

wherein M is as defined hereinabove.

In some embodiments, the chiral base is an ephedrine salt, i.e.:

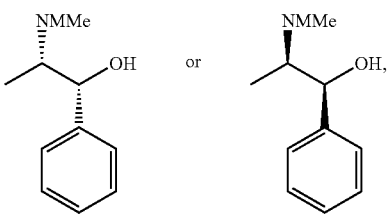

wherein M is as defined hereinabove. Thus, in one embodiment, the chiral base is a salt of (1R,2S)-(−)-ephedrine:

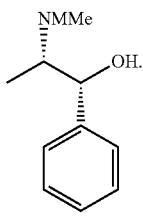

In another embodiment, the chiral base is a salt of (1S,2R)-(−)-ephedrine:

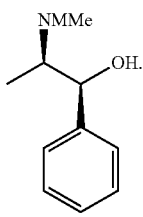

An example of "M" in all of these embodiments is lithium ion.

In another embodiment, the leaving group LG in $R^3LG$ is selected from the group consisting of Cl, Br, I, —OS(O)$_2$CH$_3$, —OS(O)$_2$C$_4$F$_9$, —OS(O)$_2$CF$_3$, and —OS(O)$_2$(4-CH$_3$-phenyl).

In another embodiment, the amine is selected from triethylamine, trimethylamine, triisopropyl amine, N,N,N'N'-tetramethylethylenediamine (TMEDA), N,N,N'N'-tetramethylpropylenediamine (TMPDA), and N,N,N'N'-tetramethylbutylenediamine (TMBDA). An exemplary amine in this regard is TMEDA.

In another embodiment, the solvent used in step (a) is selected from the group consisting of benzene, toluene, trifluorotoluene, xylene, chlorobenzene, dialkyl ethers, THF, dioxane, DMF, halogenated hydrocarbon solvents, ester solvents, and mixtures thereof. An exemplary solvent in this regard is toluene.

In one embodiment, the compound of Formula II is contacted with the chiral base first, followed by the alkylating agent $R^3$-LG. In another embodiment, the compound of Formula II is contacted first with the alkylating agent $R^3$-LG, followed by the chiral base.

In one embodiment, the acid in step (b) is selected from the consisting of HCl, $H_2SO_4$, $CH_3C(O)OH$, $CF_3C(O)OH$, $MeSO_3H$, and $C_6H_5SO_3H$.

In another embodiment, the acid in step (b) is $MeSO_3H$.

In one embodiment, the base in step (c) is selected from the group consisting of LiOH, NaOH, KOH, and sodium acetate.

In another embodiment, the base in step (c) is NaOH.

In one embodiment, the diastereomeric excess (de) value of the product is at least 85%, 90%, 95%, or 98%.

In view of the foregoing considerations, and the specific examples below, those who are skilled in the art will appreciate that a given selection of chiral base, amine, solvent, acid, or base can determine the chirality of the end product, and/or the de thereof. Making such a selection is well within the ambit of the skilled artisan.

Another embodiment of the present invention is a process for the preparation of a compound of formula III

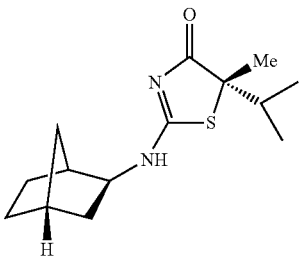 [SMILES: CC(C)[C@]1(C)SC(N[C@H]2C[C@@H]3CCC2C3)=NC1=O]

from a compound of formula IV

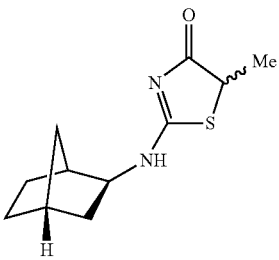 [SMILES: CC1SC(N[C@H]2C[C@@H]3CCC2C3)=NC1=O]

as described generally above.

In this embodiment, the process comprises the steps of (a) contacting compound IV with a chiral base of the following formula

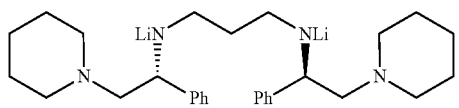

in the presence of TMEDA, and then (b) reacting the product from step (a) with isopropyl iodide.

In one embodiment, the process further comprises the steps of (c) contacting the product of step (b) with $MeSO_3H$ to form a mesylate salt; and (d) reacting the mesylate salt from step (c) with NaOH to yield the compound of formula III.

In one embodiment, the product of step (b) is of de value at least 90%, 95%, or 98%.

In another embodiment, the product of step (d) is of de value at least 99%.

Still another embodiment of the invention is a further process for the preparation of a compound according to formula III:

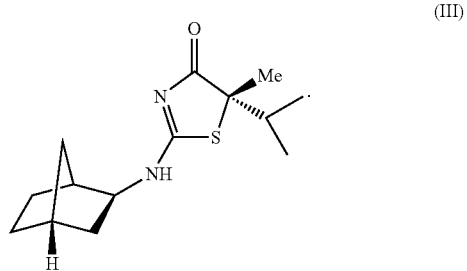 [SMILES: CC(C)[C@]1(C)SC(N[C@H]2C[C@@H]3CCC2C3)=NC1=O]

In this embodiment, the process comprises (a) contacting a compound of formula (IV)

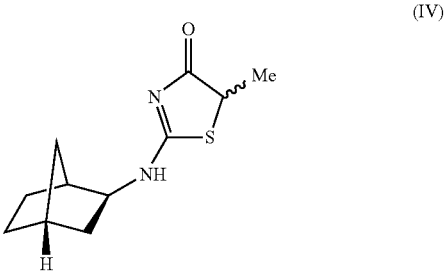 [SMILES: CC1SC(N[C@H]2C[C@@H]3CCC2C3)=NC1=O]

with a chiral base in the presence of a deprotonating reagent; and (b) reacting the product of step (a) with isopropyl iodide. The term "chiral base" as used hereinthroughout contemplates a chiral molecule that is a base. The term "chiral base" additionally contemplates a chiral base that results from deprotonation of a neutral or free base. Hence, a chiral base containing the ion "M" as defined hereinabove formally refers to a salt of the free base. A free base features —OH and —NH or —$NH_2$ groups, for instance, meaning chiral bases that are not deprotonated.

Illustrative examples of a chiral base include the following:

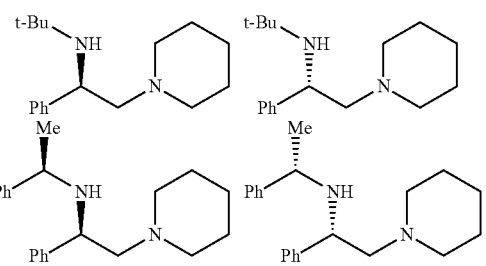

21
-continued
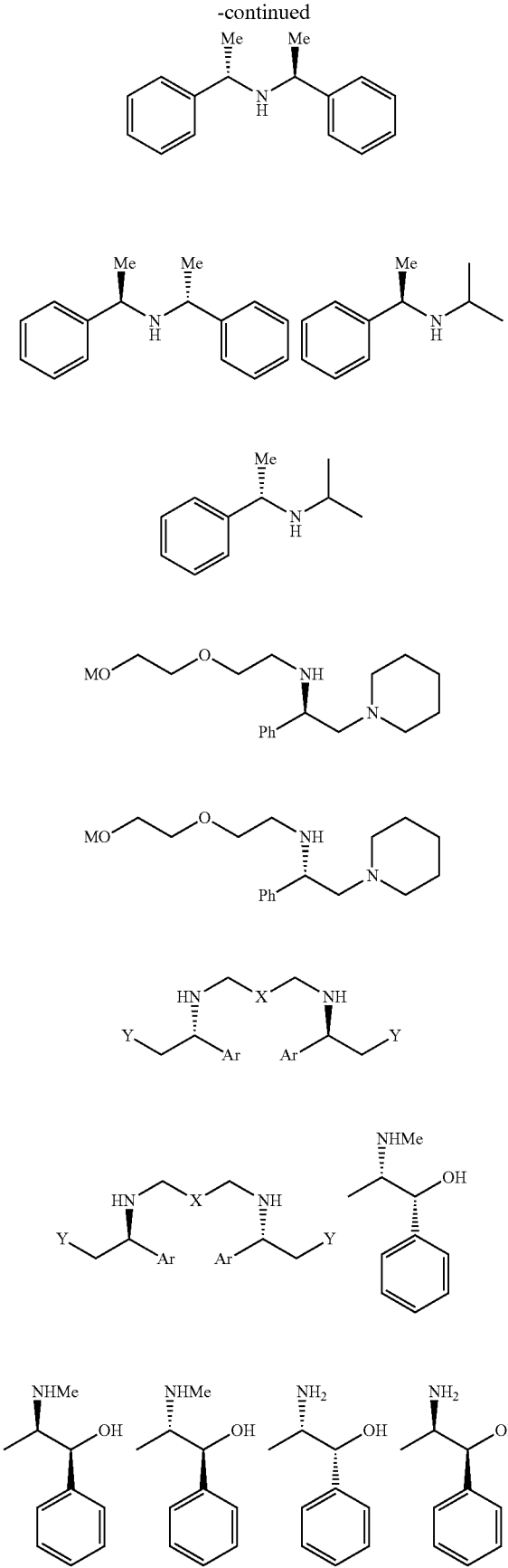
22
-continued
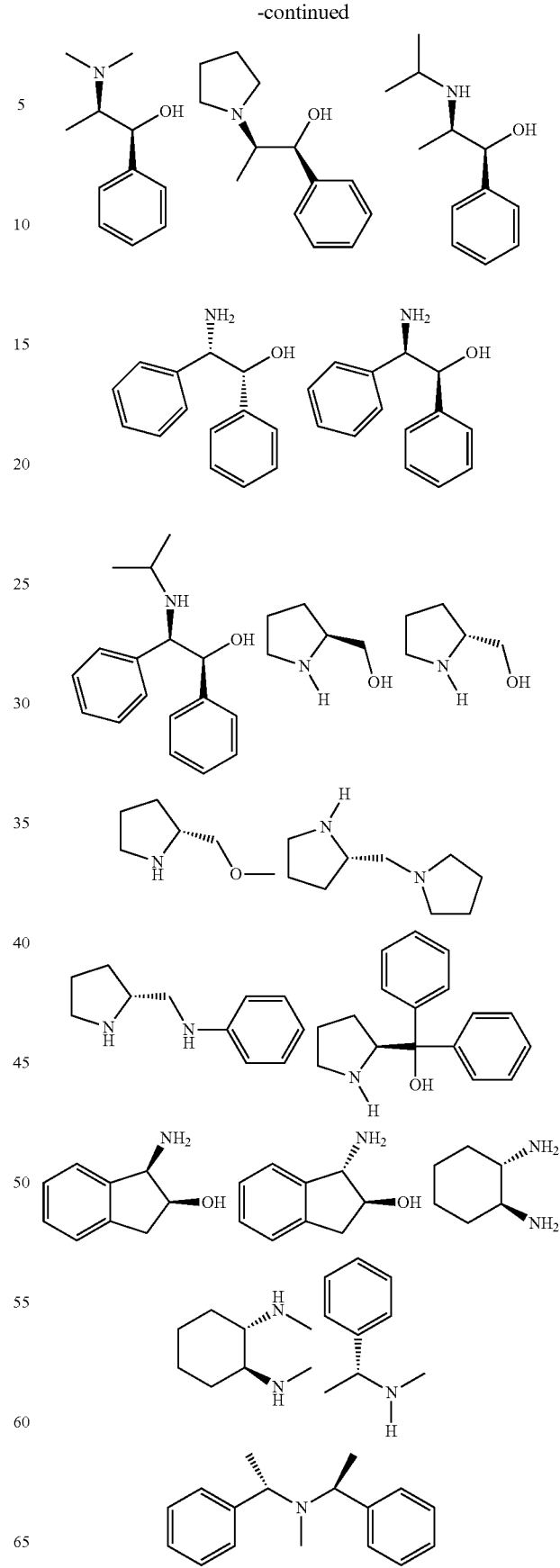

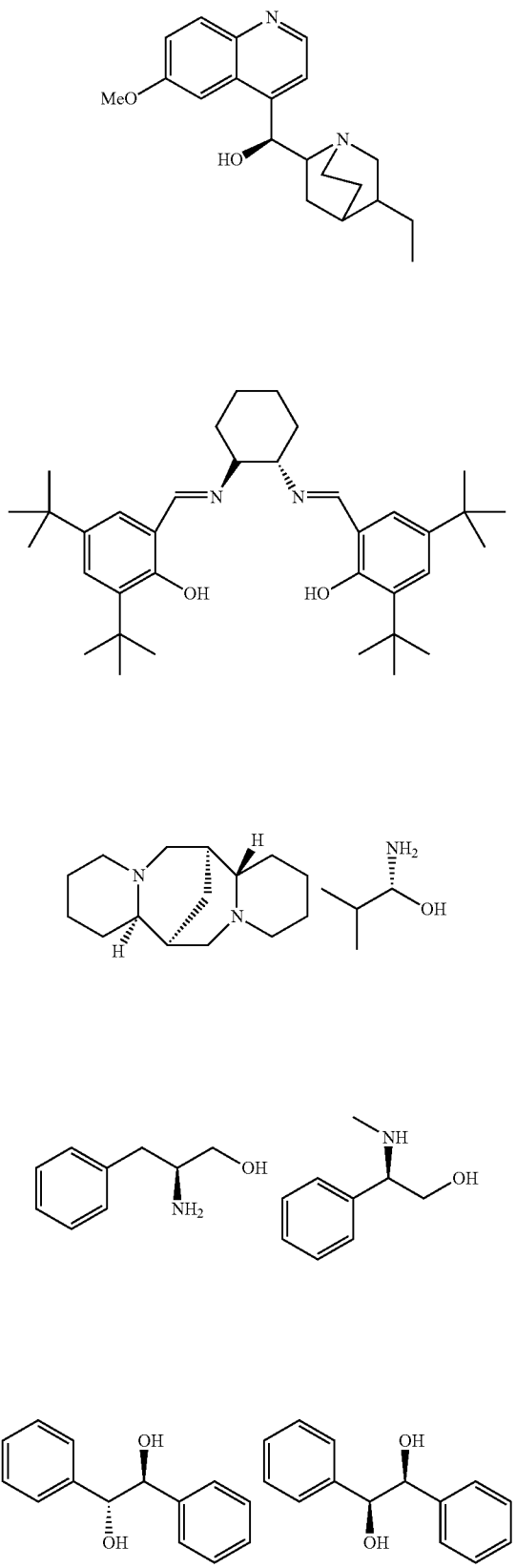

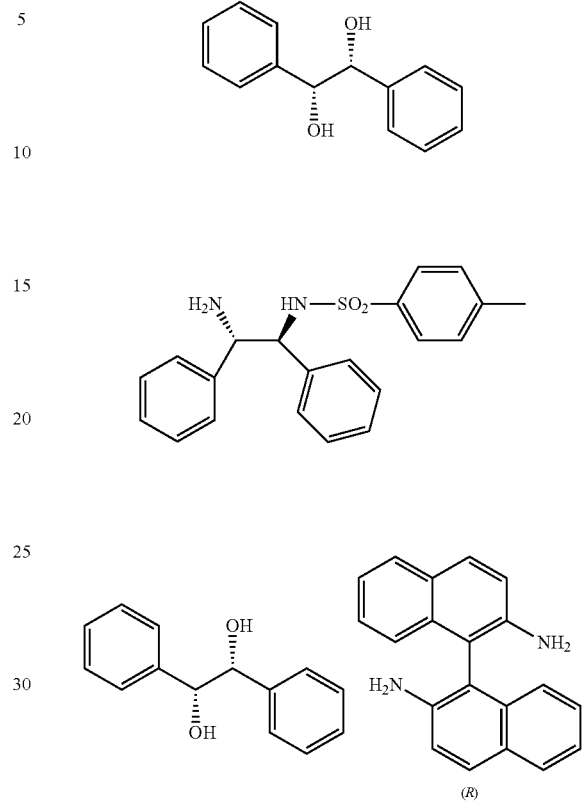

In some embodiments, the chiral base is

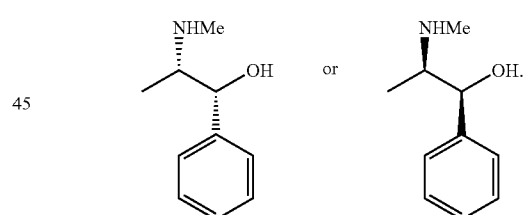

In the embodiment described above, the process can be carried out in the presence of a deprotonating agent. Many deprotonating agents are well-known to those who are skilled in the field of organic synthesis. For instance, deprotonating agents include but are not limited to metalorganics, such as alkyllithiums. Common examples of alkyllithiums are methyllithium, n-butyllithium, tert-butyllithium, and hexyllithium. Other deprotonating reagents include metal hydrides, such as, for instance, lithium hydride, sodium hydride, and potassium hydride.

The invention will now be described in reference to the following Examples. These examples are not to be regarded as limiting the scope of the present invention, but shall only serve in an illustrative manner.

EXAMPLES

Example 1

Preparation of (5S)-2-(bicyclo[2.2.1]heptan-2-ylamino)-5-methyl-5-propylthiazol-4(5H)-one (6)

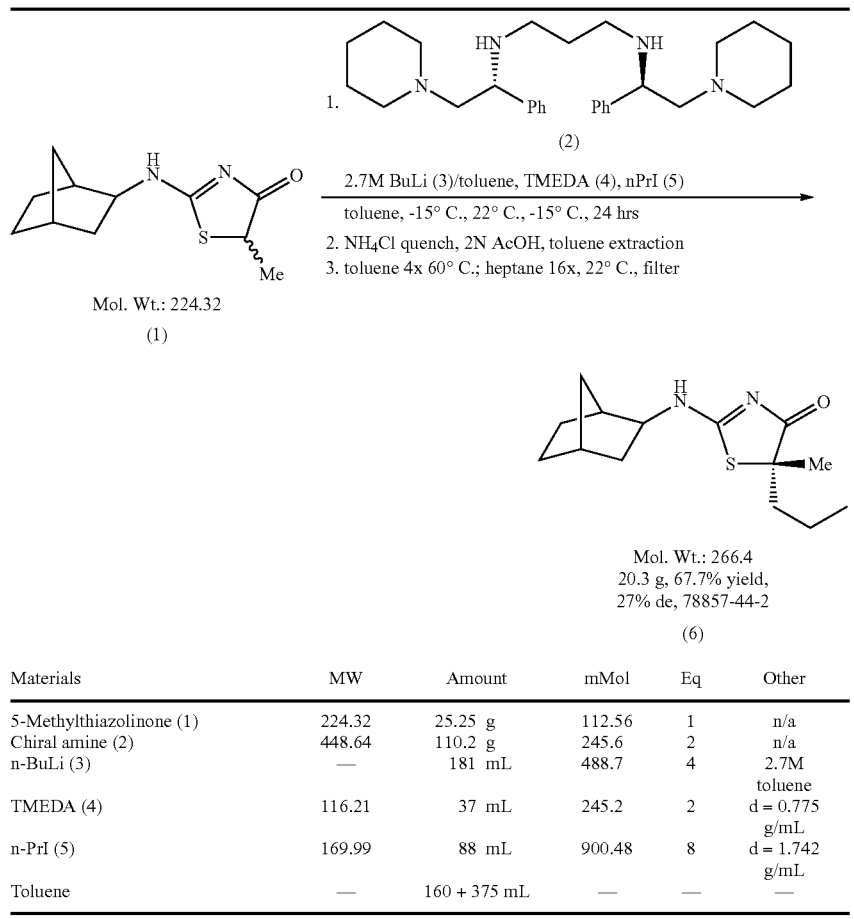

| Materials | MW | Amount | mMol | Eq | Other |
|---|---|---|---|---|---|
| 5-Methylthiazolinone (1) | 224.32 | 25.25 g | 112.56 | 1 | n/a |
| Chiral amine (2) | 448.64 | 110.2 g | 245.6 | 2 | n/a |
| n-BuLi (3) | — | 181 mL | 488.7 | 4 | 2.7M toluene |
| TMEDA (4) | 116.21 | 37 mL | 245.2 | 2 | d = 0.775 g/mL |
| n-PrI (5) | 169.99 | 88 mL | 900.48 | 8 | d = 1.742 g/mL |
| Toluene | — | 160 + 375 mL | — | — | — |

5-Methylthiazolinone (1) (25.25 g) was suspended in 500 mL of anhydrous toluene. The solvent of this slurry was distilled at 44° C. and 50 mbar reduced pressure to a total volume of 160 mL. To a jacketed 3 L reactor, equipped with a Julabo LH-50 process chiller, $N_2$ line, thermocouple, and overhead stirrer, was charged 110.2 g of chiral amine (2) solid. The reactor and contents were flushed with $N_2$. Toluene (375 mL) was charged to the purged reactor via cannula, yielding a clear solution of chiral amine (2). This solution was cooled to −15° C. Butyllithium (3) (181 mL, 2.7 M in toluene) was transferred via cannula to a 250 mL addition funnel attached to the reactor. The butyllithium (3) was added dropwise over a period of 30 minutes, with the internal temperature ("Tint") never rising above −9.0° C.

TMEDA (4) (37 mL) was charged to the reactor via syringe after Tint had been re-established at −15.5° C. After a 30 minute aging, the 160 mL slurry of 5-methylthiazolinone (1) in toluene was charged portion-wise via cannula, with the Tint never rising above −4.5° C. The Tint was then adjusted to 16° C. and the reaction was held for 1 hour. After this aging period, the Tint was readjusted to −15.5° C. N-propyl iodide (5) (88 mL) was charged via cannula over a period of 15 minutes, maintaining a Tint below −12° C. The Tint stabilized at −14.5° C. after completion of nPrI addition, and the mixture was stirred out for 16 hours.

After 16 hours, HPLC analysis indicated less than 5% residual starting material and a de of 34%. The reactor was equipped with a 250 mL addition funnel, to which was added 250 mL sat $NH_4Cl$. A fast dropwise addition of $NH_4Cl$ was established and the saturated solution was added over a period of 1.5 hours, during which time the Tint never rose above −8.0° C. After completion of the quench, the reactor contents were warmed to 22° C., and the mixture was agitated. The stirring was then halted and the layers were allowed to separate for 5 minutes, after which the bottom aqueous component was drained off. A second 250 mL sat. $NH_4Cl$ quench was performed in the manner previously mentioned. The toluene layer was then acidified with 3×200 mL 2N AcOH and the extraction performed by agitation, phase separation, and draining of the bottom aqueous layer. A final extraction was performed with 200 mL of sat. $NaHCO_3$ by the method previously outlined. The toluene layer post workup was then polish filtered, yielding 800 mL of a clear solution.

The total volume of the 800 mL toluene solution was reduced to 100 mL by removing the toluene under reduced pressure (40° C., 60 mbar, rotary evaporator). This concentrated toluene solution was transferred to a 3 neck 1 L round bottom flask, followed by a 10 mL toluene wash. After heating the mixture to 60° C., heptane (400 mL) was added via a 1L addition funnel over a period of 35 minutes. After completion of heptane addition the homogeneous solution was slowly cooled to 22° C. over 2 hours, resulting in a fine slurry. An additional 1 L of heptane was charged to the slurry, and the mixture was allowed to stir at 22° C. for 48 hours. After this time the slurry was filtered on a medium porosity 300 mL sinter funnel, washed with 50 mL of 0° C. heptane, and dried using house vacuum accompanied with an $N_2$ sweep for 16 hours. After this drying period the weight of the recovered solids was 20.3 g (67.7 yield), with an LCAP of >98% and a de=27%. $^1$H NMR [$(CD_3)_2SO$] δ: 9.00 (d, 1H), 3.75 (m, 1H), 2.24 (m, 1H), 2.20 (m, 1H), 1.68 (m, 3H), 1.47 (comp m, 8H), 1.12 (m, 4H), and 0.84 ppm (m, 3H).

Example 2

Preparation of (5S)-2-(bicyclo[2.2.1]hept-5-en-2-ylamino)-5-methyl-5-propylthiazol-4(5H)-one (8)

overhead stirrer, was charged 110.2 g of chiral amine (2) solid. The reactor and contents were flushed with $N_2$. Toluene (375 mL) was charged to the purged reactor via cannula, yielding a clear solution of chiral amine (2). This solution was cooled to −15° C. Butyllithium (3) (181 mL, 2.7 M in toluene) was transferred via cannula to a 250 mL addition funnel attached to the reactor. The butyllithium was added dropwise over a period of 45 minutes, with the Tint never rising above −8.0° C. TMEDA (4) (37 mL) was charged to the reactor via syringe after the Tint had been re-established at −15.5° C. After a 20 minute aging, the 160 mL slurry of thiazalinone (7) in toluene was charged portionwise via cannula, with the Tint never rising above −13° C. The Tint was then adjusted to 16° C. and the reaction was held for 30 minutes. After this aging period, the Tint was readjusted to −15.5° C. N-propyl iodide (5) (88 mL) was charged via cannula over a period of 20 minutes, maintaining a Tint below −12° C. The Tint stabilized at −14.5° C. after completion of nPrI addition, and was stirred out for 16 hours.

After 16 hours HPLC analysis indicated less than 1% residual starting material and a de of 41%. The reactor was equipped with a 250 mL addition funnel, to which was added

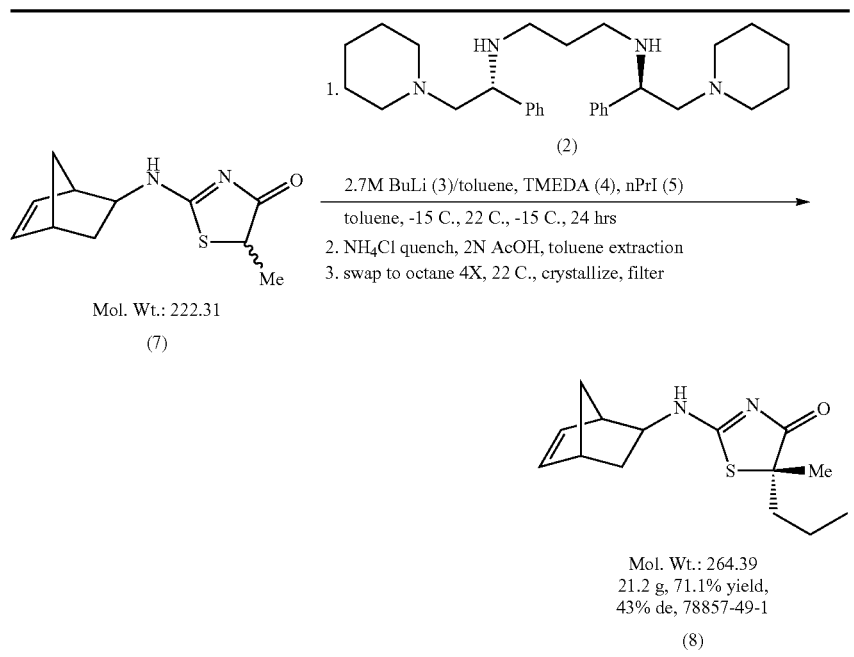

| Materials | MW | Amount | mMol | Eq | Other |
|---|---|---|---|---|---|
| 5-Methylthiazolinone (7) | 222.31 | 25.0 g | 112.56 | 1 | n/a |
| Chiral amine (2) | 448.64 | 110.2 g | 245.6 | 2 | n/a |
| n-BuLi (3) | — | 181 mL | 488.7 | 4 | 2.7M toluene |
| TMEDA (4) | 116.21 | 37 mL | 245.2 | 2 | d = 0.775 g/mL |
| n-PrI (5) | 169.99 | 88 mL | 900.48 | 8 | d = 1.742 g/mL |
| Toluene | — | 160 + 375 mL | — | — | — |

Procedure:

5-Methylthiazolinone (7) (25.0 g) was suspended in 480 mL of anhydrous toluene. The solvent of this slurry was distilled at 44° C. and 50 mbar reduced pressure to a total volume of 160 mL. To jacketed 3 L reactor, equipped with a Julabo LH-50 process chiller, $N_2$ line, thermocouple, and 250 mL sat $NH_4Cl$. A fast dropwise addition of $NH_4Cl$ was established and the saturated solution was added over a period of 1.5 hours, during which time the Tint never rose above −8.0° C. After completion of the quench, the reactor contents were warmed to 22° C., and the mixture was agitated. The stirring was then halted and the layers were allowed to separate for 5 minutes, after which the bottom aqueous component was drained off. A second 250 mL sat. NH₄Cl quench was performed in the manner previously mentioned. The toluene layer was then acidified with 3×200 mL 2N AcOH and the extraction performed by agitation, phase separation, and draining of the bottom aqueous layer. A final extraction was performed with 200 mL of sat. NaHCO₃ by the method previously outlined. The toluene layer post workup was then polish filtered, yielding 775 mL of a clear solution.

The clear toluene solution was concentrated to 100 mL at 50 C and 60 mbar, after which anhydrous octane (400 mL) was charged to the flask. This mixture was concentrated at 60° C. and 80 mbar to ~100 mL total volume, and was then diluted to 400 mL with octane. This solution was slowly cooled to 22° C., yielding a slurry that was stirred for 2 hours. The slurry was filtered on a medium porosity sinter funnel and dried under house vacuum overnight with an N₂ sweep, yielding 11.3 g of solids. The 350 mL of remaining mother liquor was concentrated down to 50 mL total volume (60° C., 70 mbar) and upon cooling to 22° C. a white solid rapidly crashed out. This solid was filtered in the same manner of the first batch, yielding 9.9 g of a white solid. Combination of both precipitates afforded 21.2 g (71.1% yield) of solids, 90% LCAP, de=43%. ¹H NMR [(CD₃)₂SO] δ: 9.26 (d, 1H), 6.21 (m, 1H), 6.09 (m, 1H), 3.75 (m, 1H), 2.86 (m, 1H), 2.78 (d, 1H), 1.54 (comp m, 10H), 1.04 (m, 1H), and 0.86 ppm (m, 3H). Note: a minor isomer was also visible by ¹H NMR.

Example 3

Preparation of (S)-5-isopropyl-5-methyl-2-((S)-1-phenylethylamino)thiazol-4(5H)-one (11)

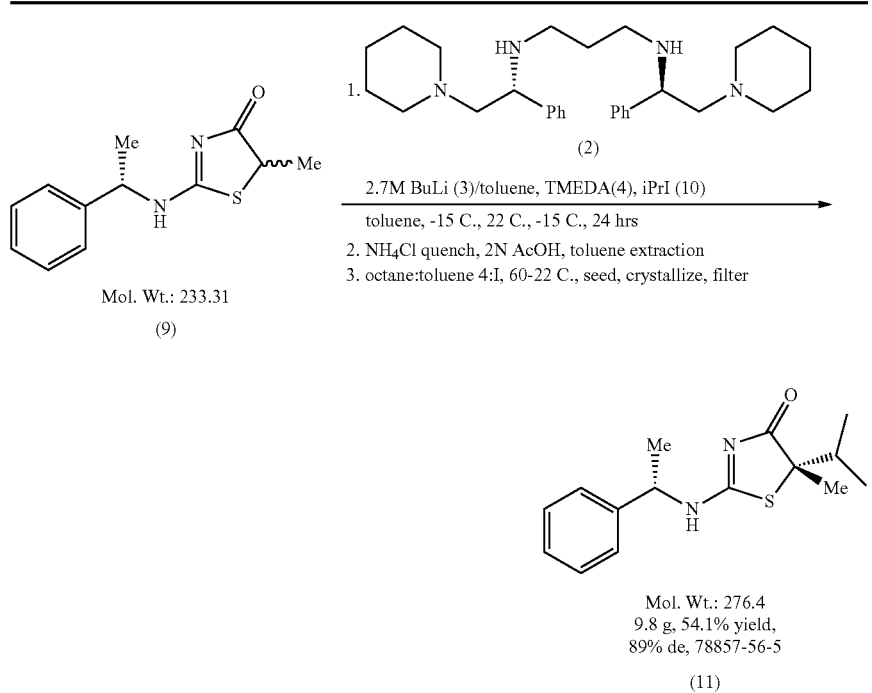

| Materials | MW | Amount | mMol | Eq | Other |
|---|---|---|---|---|---|
| 5-Methylthiazolinone (9) | 233.31 | 26.3 g | 112.56 | 1 | 96.9% de |
| Chiral amine (2) | 448.64 | 110.2 g | 245.6 | 2 | n/a |
| n-BuLi (3) | — | 181 mL | 488.7 | 4 | 2.7M toluene |
| TMEDA (4) | 116.21 | 37 mL | 245.2 | 2 | d = 0.775 g/mL |
| i-PrI (10) | 169.99 | 90 mL | 900.48 | 8 | d = 1.70 g/mL |
| Toluene | — | 160 + 375 mL | — | — | — |

Procedure:

5-Methylthiazolinone (9) (26.3 g) was suspended in 480 mL of anhydrous toluene. The solvent of this slurry was distilled at 44 C and 50 mbar reduced pressure to a total volume of 160 mL. To jacketed 3 L reactor, equipped with a Julabo LH-50 process chiller, $N_2$ line, thermocouple, and overhead stirrer, was charged 110.2 g of chiral amine (2) solid. The reactor and contents were flushed with N2. Toluene (375 mL) was charged to the purged reactor via cannula, yielding a clear solution of chiral amine (2). This solution was cooled to −15° C. Butyllithium (3) (181 mL, 2.7 M in toluene) was transferred via cannula to a 250 mL addition funnel attached to the reactor. The butyllithium was added dropwise over a period of 45 minutes, with the Tint never rising above −8.0° C. TMEDA (4) (37 mL) was charged to the reactor via syringe after the Tint had been re-established at −16.5° C. After a 20 minute aging, the 160 mL slurry of thiazalinone (9) in toluene was charged portionwise via cannula, with the Tint never rising above −13° C. The Tint was then adjusted to 16° C. and the reaction was held for 30 minutes. After this aging period, the Tint was readjusted to −16.5° C. I-propyl iodide (10) (90 mL) was charged via cannula over a period of 20 minutes, maintaining a Tint below −14° C. The Tint stabilized at −14.5° C. after completion of iPrI addition, and was stirred out for 16 hours.

After 16 hours, HPLC analysis indicated less than 3% residual starting material and a de of 85.8%. The reactor was equipped with a 250 mL addition funnel, to which was added 250 mL sat $NH_4Cl$. A fast dropwise addition of $NH_4Cl$ was established and the saturated solution was added over a period of 1.5 hours, during which time the Tint never rose above −7.0° C. After completion of the quench, the reactor contents were warmed to 22° C., and the mixture was agitated. The stirring was then halted and the layers were allowed to separate for 5 minutes, after which the bottom aqueous component was drained off. A second 250 mL sat. $NH_4Cl$ quench was performed in the manner previously mentioned. The toluene layer was then acidified with 3×200 mL 2N AcOH and the extraction performed by agitation, phase separation, and draining of the bottom aqueous layer. A final extraction was performed with 200 mL of sat. $NaHCO_3$ by the method previously outlined. The toluene layer post workup was then polish filtered, yielding 630 mL of a clear solution.

This toluene layer was concentrated under reduced pressure (50 C and 60 mbar) to a total volume of 90 mL. Octane (90 mL) was charged, and the murky mixture was concentrated to 50 mL total volume under the aforementioned conditions. This cycle of octane dilution to the mixture (90 mL each cycle) was performed until the ratio of octane to toluene was 4:1 by $^1H$ NMR. The mixture was heated to 65 C (clear solution), and slowly cooled to 35 C, at which point seed (50 mg) was suspended in the cloudy solution. The resulting slurry was cooled to 22° C. over a period of 2 hours and held 13 hours stirring under N2. Two additional 100 mL portions of octane were charged individually via an addition funnel, and after 2.5 hours of vigorous stirring the slurry was filtered. The solids were dried 16 hours with house vacuum under an $N_2$ sweep. A light brown solid was obtained (9.8 g, 54.1% yield), LCAP 99%, de of 89.1%. $^1H$ NMR [$(CD_3)_2SO$] δ: 9.61 (d, 1H), 7.32 (comp m, 5H), 5.19 (m, 1H), 1.95 (m, 1H), 1.50-1.45 (comp m, 6H), 0.95-0.56 (comp m, 6H). Note: a minor isomer was also visible by $^1H$ NMR.

Example 4

Preparation of (S)-5-methyl-2-((S)-1-phenylethylamino)-5-propylthiazol-4(5H)-one (12)

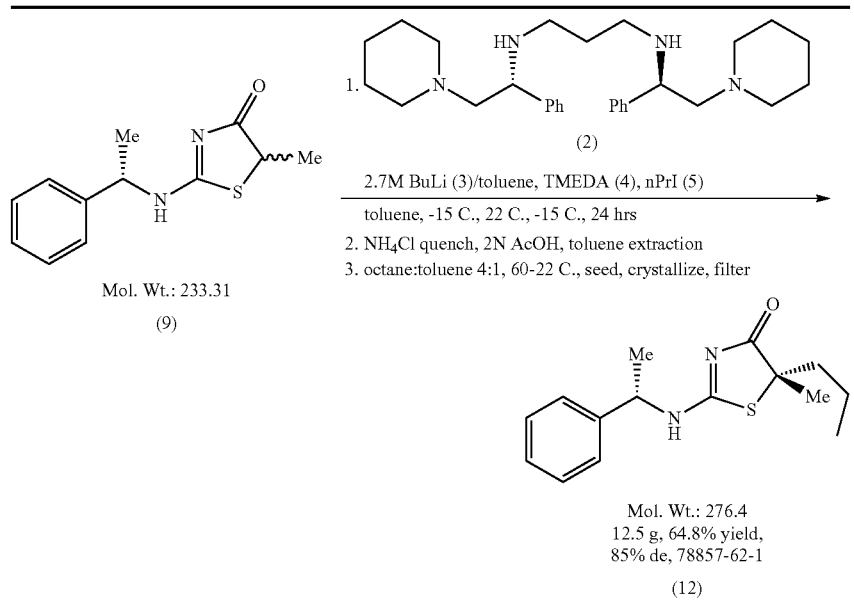

| Materials | MW | Amount | mMol | Eq | Other |
|---|---|---|---|---|---|
| 5-Methylthiazolinone (9) | 233.31 | 26.3 g | 112.56 | 1 | 96.9% de |
| Chiral amine (2) | 448.64 | 110.2 g | 245.6 | 2 | 68628-85-2 |
| n-BuLi (3) | — | 181 mL | 488.7 | 4 | 2.7M |
| TMEDA (4) | 116.21 | 37 mL | 245.2 | 2 | d = 0.775 g/mL |
| n-PrI (5) | 169.99 | 88 mL | 900.48 | 8 | d = 1.742 g/mL |
| Toluene | — | 160 + 375 mL | — | — | — |

Procedure:

5-Methylthiazolinone (9) (26.3 g) was suspended in 500 mL of anhydrous toluene. The solvent of this light slurry was distilled at 44 C and 50 mbar reduced pressure to a total volume of 160 mL. To jacketed 3 L reactor, equipped with a Julabo LH-50 process chiller, $N_2$ line, thermocouple, and overhead stirrer, was charged 110.2 g of chiral amine (2) solid. The reactor and contents were flushed with $N_2$. Toluene (375 mL) was charged to the purged reactor via cannula, yielding a clear solution of chiral amine (2). This solution was cooled to −15° C. Butyllithium (3) (181 mL, 2.7 M in toluene) was transferred via cannula to a 250 mL addition funnel attached to the reactor. The butyllithium (3) was added dropwise over a period of 45 minutes, with the Tint never rising above −11.5 C. TMEDA (4) (37 mL) was charged to the reactor via syringe after the Tint had been re-established at −16.5 C. After a 10 minute aging, the 160 mL slurry of thiazalinone (9) in toluene was charged portionwise via cannula, with the Tint never rising above −8.5° C. The Tint was then adjusted to 16° C. and the reaction was held for 50 minutes. After this aging period, the Tint was readjusted to −17.0 C. N-propyl iodide (5) (88 mL) was charged via cannula over a period of 20 minutes, maintaining a Tint below −14 C. The Tint stabilized at −14.5° C. after completion of nPrI addition, and was stirred out for 16 hours.

After 16 hours, HPLC analysis indicated less than 0.5% residual starting material and a de of 61.2%. The reactor was equipped with a 250 mL addition funnel, to which was added 250 mL sat $NH_4Cl$. A fast dropwise addition of $NH_4Cl$ was established and the saturated solution was added over a period of 1.5 hours, during which time the Tint never rose above −3.1° C. After completion of the quench, the reactor contents were warmed to 22° C., and the mixture was agitated. The stirring was then halted and the layers were allowed to separate for 5 minutes, after which the bottom aqueous component was drained off. A second 250 mL sat. $NH_4Cl$ quench was performed in the manner previously mentioned. The toluene layer was then acidified with 3×200 mL 2N AcOH and the extraction performed by agitation, phase separation, and draining of the bottom aqueous layer. A final extraction was performed with 200 mL of sat. $NaHCO_3$ by the method previously outlined. The toluene layer post workup was then polish filtered, yielding 750 mL of a clear solution.

This toluene layer was concentrated under reduced pressure (60° C. and 80 mbar) to a total volume of 90 mL. Octane (90 mL) was charged, and the murky mixture was concentrated to 60 mL total volume under the aforementioned conditions. This cycle of octane dilution to the mixture (90 mL each cycle) was performed until the ratio of octane to toluene was 2:1 by $^1H$ NMR. The toluene/octane solution (60 mL total volume) was heated to 70° C., achieving a clear solution. After achieving a Tint of 53° C., 50 mg of seed were charged. The slurry was cooled to 33° C. over a period of 20 minutes then reheated to 70° C. over 35 minutes. This mixture was then cooled to 43.5° C. over 2 hours, and octane (160 mL) was charged to the slurry in a fast dropwise addition over 30 minutes. The slurry was then cooled to 22° C. and held 16 hours stirring under $N_2$. The slurry was filtered and dried under house vacuum with an $N_2$ sweep for 4 hours, yielding 12.5 g (64.8% yield) of light brown solids, 98% LCAP, de=85.7%. $^1H$ NMR [$(CD_3)_2SO$] δ: 9.60 (d, 1H), 7.33 (comp m, 5H), 5.19 (m, 1H), 1.68 (m, 2H), 1.46-1.43 (comp m, 7H), 1.06 (m, 1H), 0.86 (comp m, 3H). Note: a minor isomer was also visible by $^1H$ NMR.

Example 5

Preparation of (5S)-2-(bicyclo[2.2.1]heptan-2-ylamino)-5-methyl-5-propylthiazol-4(5H)-one (6) of high diastereomeric excess

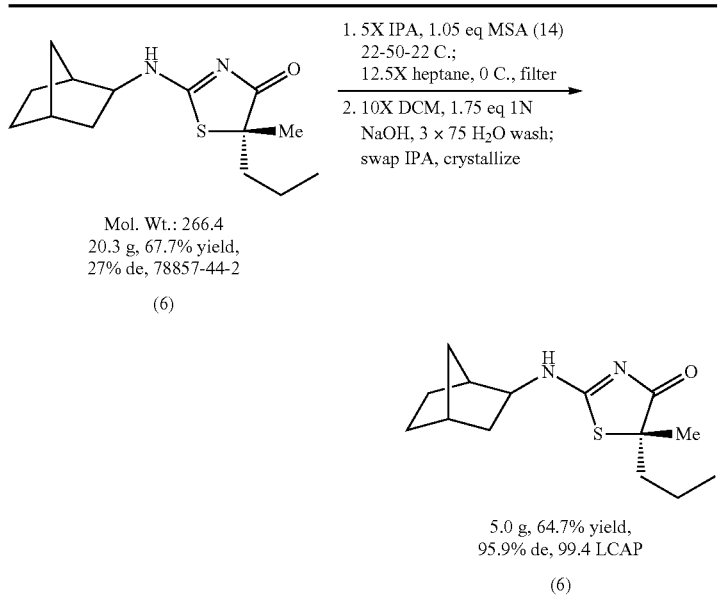

| Materials | MW | Amount | mMol | Eq | Other |
|---|---|---|---|---|---|
| 5-Me/nPr Thiazalinone (6) | 266.4 | 20.3 g | 76.0 | 1 | n/a |
| 5-Me/nPr Thiazalinone MSA salt (13) | 362.51 | 10.6 g | 29.2 | 1 | n/a |
| Methanesulfonic Acid (14) | 96.11 | 5.2 mL | 80.0 | 1.05 | d = 1.481 g/mL |

| | | | | | |
|---|---|---|---|---|---|
| -continued | | | | | |
| IPA | — | 100 mL | — | — | 5X |
| DCM | — | 100 mL | — | — | 10X |
| NaOH aq | — | 50 mL | 50.0 | 1.75 | 1M |

Procedure:

To a 250 mL 1 neck round bottom flask was suspended 20.4 g of crude 5-Me/nPr thiazalinone (6) in 100 mL dry isopropanol at 22° C. To this slurry was added methanesulfonic acid (14) (5.2 mL, 1.05 eq), which upon complete addition fully dissolved the solids yielding a homogeneous solution. Heated over a period of 25 minutes to 50 C, held for 1 hour, then cooled to 22° C. and held 16 hours under N2. After this period the still homogeneous solution was transferred to a 500 mL 3 neck round bottom flask fitted with an overhead stirrer and a 500 mL addition funnel. Heptane (285 mL) was added portion wise, after which the 22° C. mixture was cooled in an ice bath. After 10 minutes (Tint=8.2 C) 100 mg of seed in a 12× slurry in heptane was added. The mixture was held for 16 hours and allowed to slowly warm to 22° C., resulting in a thick white slurry. This was filtered and dried (house vacuum/N₂ sweep) for 5 hours to yield 10.6 g of the MSA salt (13), 95.1% de, mother liquor de=−42.7%. ¹H NMR [(CD₃)₂SO] δ: ¹H NMR [(CD₃)₂SO] δ: 9.36 (d, 1H), 3.75 (m, 1H), 2.34 (s, 3H), 2.24 (m, 1H), 2.20 (m, 1H), 1.68 (m, 3H), 1.47 (comp m, 8H), 1.12 (m, 4H), and 0.84 ppm (m, 3H). Note: a minor isomer was also visible by ¹H NMR.

To a 250 Erlenmeyer flask was added 10.6 g of the 5-Me/nPr thiazalinone MSA salt (13). This solid was subsequently dissolved with 100 mL dry DCM, yielding a clear 10× solution. NaOH (1N, 50 mL) was charged to this solution and stirred vigorously for 20 minutes. After halting agitation the biphasic system was transferred to a 250 mL separatory funnel, and the upper aqueous layer was removed. Three water washes (75 mL each) were performed on the organic layer, the pH of the final water layer being 6.5-7.0. The DCM layer was polish filtered into a 250 mL round bottom flask (100 mL total), and concentrated down to 20 mL total volume (40° C., 60 mbar). Isopropanol (100 mL) was charged to this solution and the total volume was concentrated to 20 mL. An additional 20 mL of IPA was charged to the flask to obtain a 3.75× solution of the free base in IPA. Upon cooling this mixture from the evaporator bath temp of 40 C, a white solid precipitated. This was filtered and dried to yield 5.0 g of the product, 64.7% recovery, 99.4% LCAP and 95.9% de. ¹H NMR [(CD₃)₂SO] δ: 9.00 (d, 1H), 3.75 (m, 1H), 2.24 (m, 1H), 2.10 (m, 1H), 1.68 (m, 3H), 1.47 (comp m, 8H), 1.12 (m, 4H), and 0.84 ppm (m, 3H).

Example 6

Preparation of (5S)-2-(bicyclo[2.2.1]hept-5-en-2-ylamino)-5-methyl-5-propylthiazol-4(5H)-one of high diastereomeric excess

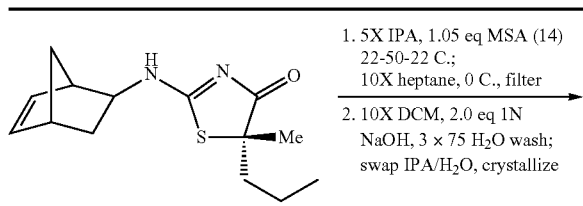

Mol. Wt.: 264.39
21.2 g, 71.1% yield,
43% de, 78857-49-1

(8)

1. 5X IPA, 1.05 eq MSA (14)
22-50-22 C.;
10X heptane, 0 C., filter 2. 10X DCM, 2.0 eq 1N
NaOH, 3 × 75 H₂O wash;
swap IPA/H₂O, crystallize

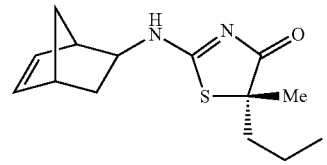

9.4 g, 73.0% yield,
93.1% de, 89.0 LCAP (8)

| Materials | MW | Amount | mMol | Eq | Other |
|---|---|---|---|---|---|
| 5-Me/nPr Thiazalinone (8) | 264.39 | 21.2 g | 80.2 | 1 | n/a |
| 5-Me/nPr Thiazalinone MSA salt (15) | 360.49 | 17.5 g | 49.0 | 1 | n/a |
| Methanesulfonic Acid (14) | 96.11 | 5.5 mL | 84.2 | 1.05 | d = 1.481 g/mL |
| IPA | — | 100 mL | — | — | 5X |
| DCM | — | 175 mL | — | — | 10X |
| NaOH aq | — | 88 mL | 88.0 | 2.00 | 1M |

Procedure:

To a 250 mL 1 neck round bottom flask was suspended 20.4 g of crude 5-Me/nPr thiazalinone (8) in 100 mL dry isopropanol at 22° C. To this thick, pearl white slurry was added methanesulfonic acid (14) (5.5 mL, 1.05 eq), which upon complete addition fully dissolved the solids yielding a homogeneous solution. The mixture was heated over a period of 15 minutes to 50° C., held for 35 minutes, then cooled to 22° C. and held 16 hours under $N_2$. After this period the still homogeneous solution was transferred to a 1 L 3 neck round bottom flask fitted with an overhead stirrer and a 500 mL addition funnel. Heptane (268 mL, 2× with respect 134 mL total IPA solution) was added portion wise over 15 minutes, after which the 22° C. mixture was cooled in an ice bath. After 50 minutes the mixture was warmed to 22° C., and the thick white slurry was aged for 16 hours. This was filtered and dried (house vacuum/N2 sweep) for 5 hours, affording 17.5 g of the MSA salt (15) 73.0% yield, 99.1% purity, 82.2% de. $^1$H NMR [$(CD_3)_2SO$] δ: 9.40 (d, 1H), 6.21 (m, 1H), 6.09 (m, 1H), 3.74 (m, 1H), 2.87 (m, 1H), 2.81 (m, 1H), 2.31 (s, 3H), 1.54 (comp m, 10H), 1.04 (m, 1H), and 0.86 ppm (m, 3H).

To a 500 Erlenmeyer flask was added 17.5 g of the 5-Me/nPr thiazalinone MSA salt (15). This solid was subsequently suspended in 175 mL of dry DCM to afford a slurry. Sodium hydroxide (1 M, 88 mL) was charged to the slurry and the biphasic mixture was stirred vigorously for 16 hours. After this period the biphasic mixture was transferred to a 1 L separatory funnel, allowing 5 minutes for phase separation. The basic aqueous layer was drained away from the organic phase, after which 3×130 mL $H_2O$ washes were performed on the DCM layer. The pH of the final aqueous was 7.0. The DCM layer was polished filtered and concentrated to 20 mL total volume. IPA (3.75×, 65 mL total) was charged and the entire mixture was concentrated to 20 mL total volume (40° C., 60 mbar). An additional 105 mL of IPA was charged and this solution was concentrated to 65 mL total volume (3.75× IPA). This mixture was then heated to 70° C., and then slowly cooled to 0 C. When the Tint was 66° C. water (52 mL) was charged portion-wise over a period of 5 minutes. When Tint=30.0 C a white slurry was achieved. This white slurry was stirred at 22° C. for 16 hours under $N_2$. After this period the slurry was cooled at 0° C., filtered, and washed with 70 mL of 60:40 $H_2O$:IPA solution. The solids were dried on a medium porosity frit for 4 hours under an $N_2$ sweep, affording 9.4 g (73% recovery) of a white solid, 89% LCAP, 93.1% de. $^1$H NMR [$(CD_3)_2SO$] δ: 9.26 (d, 1H), 6.21 (m, 1H), 6.09 (m, 1H), 3.75 (m, 1H), 2.86 (s, 114), 2.80 (s, 1H), 1.54 (comp m, 10H), 1.04 (m, 1H), and 0.86 ppm (m, 3H). Note: a minor isomer was also visible by $^1$H NMR.

Example 7

Preparation of (5S)-2-(bicyclo[2.2.1]heptan-2-ylamino)-5-isopropyl-5-methylthiazol-4(5H)-one (19) of high diastereomeric excess Step 1:

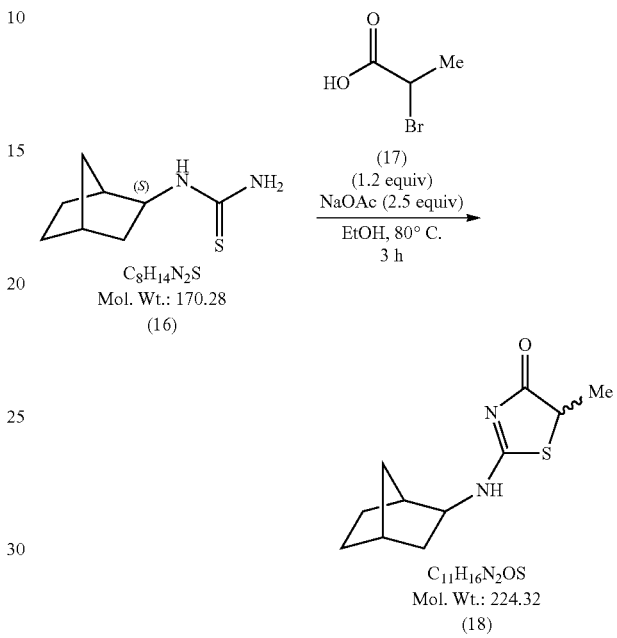

A 20 L reactor was assembled as described in the "Equipment" section (above) and placed under a nitrogen sweep. (S)-exo-2-norbornylthiourea (16) (801.4 g) was charged to the reactor followed by 3.0 L of absolute ethanol. Agitation was initiated (142 RPM) and this was followed by addition of 2-bromopropionic acid (17) (509 mL) via graduated cylinder. The graduated cylinder was rinsed with 400 mL of absolute ethanol and the rinse was transferred to the reactor. Sodium acetate (965.7 g) was then charged and this was followed by a final charge of 1.4 L of absolute ethanol. The reaction mixture was heated to 80° C. and aged at this temperature for 3 hours, after which it was cooled to 22° C. Deionized water (13 L) was added and a small exotherm resulted. The mixture was allowed to return to 22° C. and aged for 12 h. The resulting suspension was filtered through a medium-porosity sintered glass funnel. NOTE: At this stage, crude material was combined during filtration with crude product from a parallel reaction with 234 g of thiourea. This was necessary due to the capacity limit of the 20 L reactor.

The solid remaining in the reactor was rinsed into the funnel with deionized water (2 L) and the filter cake was washed with 1 L of deionized water. The solid was air-dried on the filter for 3 hours, then transferred to drying trays and dried at 50° C. and 15 torr until TGA analysis indicated water content of less than 3.0%. The dry weight was recorded (1311 g) and the solid was transferred to a clean 20 L jacketed reactor. MTBE (5.9 L) was added and agitation was initiated (120 RPM). The slurry was heated to 50° C. and aged at this temperature for 2 h. The mixture was then cooled to 22° C. and filtered through a medium-porosity sintered glass funnel. The collected solid was washed twice with MTBE (500 mL each wash) and air-dried on the funnel for 1 h. The material was transferred to drying trays and dried at 50° C. and 15 torr until TGA analysis registered water content of less than 1.0%. The dried solid was packaged (isolated 1240 g, 91% yield, >98 A %).

Step 2: Asymmetric alkylation

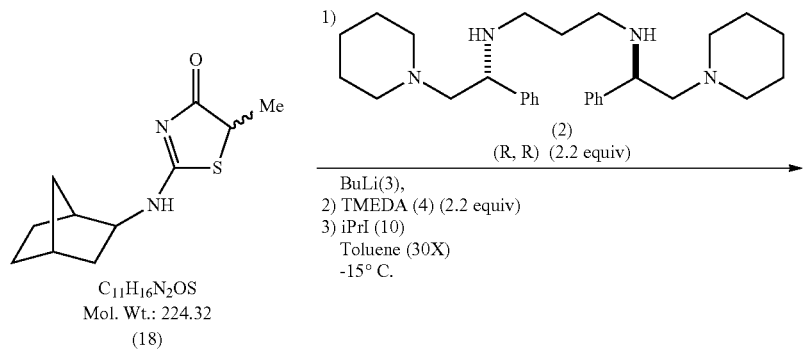

A 20 L reactor was placed under a nitrogen sweep. (R,R)-chiral amine (2) (1761.2 g) was charged to the reactor. This was followed by a nitrogen sweep for 15 minutes. Anhydrous toluene (6.0 L) was then charged and agitation was initiated. The reaction mixture was allowed to stir under a nitrogen sweep for an additional 15 minutes, after which the reaction mixture was cooled to −5° C. A 3 L dropping funnel was charged with n-BuLi (3) solution (2.9 L). Once an internal temperature of −5° C. had been achieved, dropwise addition of the n-BuLi was initiated, ensuring that internal temperature did not rise above 0° C. The reaction mixture was cooled to −15° C. and aged for 30 minutes. TMEDA (4) (592 mL) was then added via cannula. 5-methylthiazolinone (18) (400 g) was slurried in anhydrous toluene (1.6 L) in a separate 5 L, 3-neck round-bottom flask under a nitrogen sweep for 15 min. The resulting slurry was charged portionwise to the reactor via cannula, adjusting addition rate and jacket temperature so as to maintain the internal temperature below 0° C. The round-bottom flask used to prepare the substrate slurry was rinsed with toluene (2×450 mL) and the washes were charged to the reactor. The reaction mixture was warmed to 22° C. and aged at this temperature for 30 min. The mixture was then re-cooled to −15° C. Isopropyl iodide (10) (1.42 L) was charged via cannula at such a rate as to maintain temperature below −12.5° C., adjusting the jacket temperature as needed to control the resulting exotherm. An analytical sample was pulled 20 min following completion of the isopropyl iodide addition (following the sample preparation protocol in the analytical section).

The reaction mixture was allowed to age at −15° C. until >93% conversion was obtained, and then quenched by dropwise addition of saturated NH$_4$Cl solution, again adjusting addition rate and jacket temperature to control the resulting exotherm. The reaction mixture was warmed to room temperature and agitation was halted. Phases were allowed to separate (at least 20 min) and the lower aqueous layer was drained. 3.0 L of saturated NH$_4$Cl solution was added and the mixture agitated for 20 minutes. The Phases were allowed to separate and the lower aqueous layer was drained. Acetic acid solution (2 M, 3.3 L) was charged to the reactor, and the mixture agitated for 20 minutes. The phases were allowed to separate and the lower aqueous layer was drained. This acetic acid wash was repeated.

Brine (3.3 L) was charged to the reactor, and the mixture was agitated for 20 minutes. The phases were allowed to separate and the lower aqueous phase was drained. Saturated NaHCO$_3$ solution (3.3 L) was charged to the reactor slowly while agitating for 20 minutes. The phases were allowed to separate (at least 20 min) and the lower aqueous phase was drained. A second NaHCO$_3$ (3.3 L) was performed and the lower aqueous was drained. Brine (3.3 L) was again charged to the reactor, the mixture was agitated for 20 minutes. The phases were allowed to separate and the lower aqueous phase was drained.

A 200 mL sample of the crude toluene solution was reduced via vacuum distillation to a final volume of 30 mL. The resulting suspension was then maintained at a temperature of 60° C. To the suspension was added 100 mL of heptane while maintaining the temperature above 55° C. Once the addition of heptane was completed, the suspension was cooled to 5° C. over an hour period. The batch was held at 5° C. for 90 minutes. The solid was then filtered through a medium fritted glass filter and the cake was washed with a minimum amount (15 mL) of cold heptane (5° C.). The solid was dried in a vacuum oven at 55° C. for 16 hours. Isolated 5.25 g of solid (67.7% yield).

Step 3 (MSA Salting)

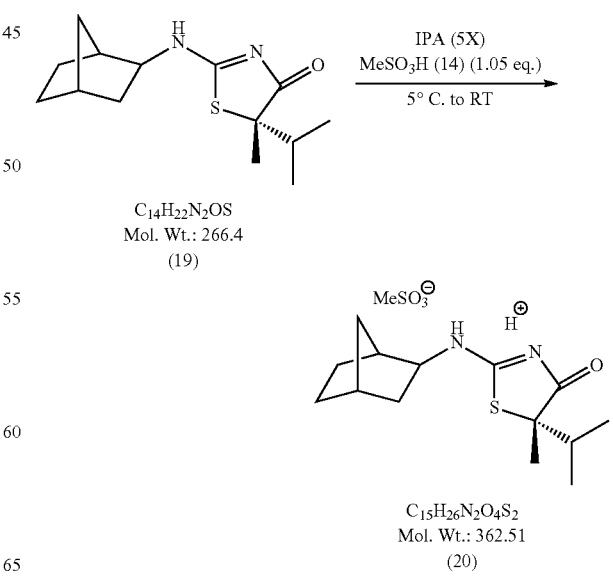

A 3-neck, 2 L round bottom flask was placed under a $N_2$ sweep. Crude alkylation product (19) (84% de; 225 g) was then charged, followed by isopropyl alcohol (1125 mL, 5 volumes). Agitation was established and methanesulfonic acid (14) (57.5 mL) was then charged via addition funnel. The reaction mixture was heated to 50° C. and aged for 1 hour. The reactor contents were then cooled to 18-25° C. and aged for 1.5 hours. The solid was then isolated by filtration with a Buchner funnel. An additional portion of isopropyl alcohol (338 mL, 1.5 volumes) was used to rinse any remaining solid material from the 2 L round bottom flask. The wet cake was allowed to dry on the funnel for at least 1 hour. The solid material was then transferred to a drying tray and placed in a vacuum oven at 50° C. for 16 hours. Obtained 272.2 g (88.9% uncorrected yield, 95.98% de) of dry compound (20).

Step 4 (Free Basing)

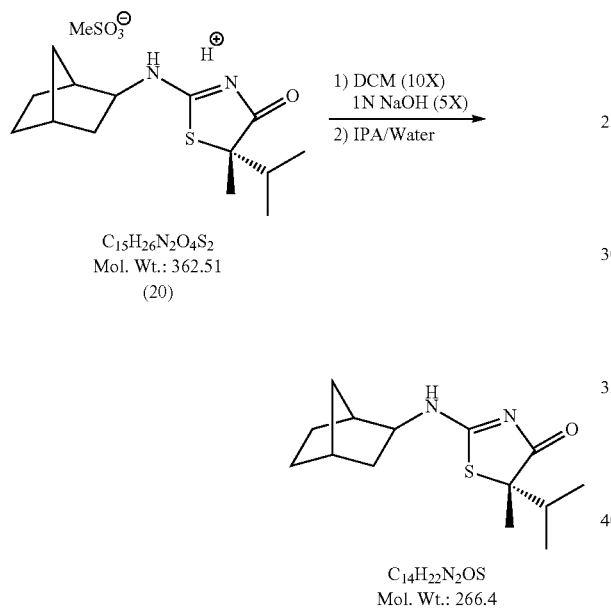

To a 40 g suspension of MSA salt (20) in DCM (10×, 400 mL) in a 1000 mL, 3 neck round bottom flask, equipped with a mechanical stirrer and a nitrogen inlet, was added 5× of 1N NaOH (200 mL). The mixture was stirred for 1 hour and transferred to a separatory funnel. The layers were allowed to settle for 15 minutes and then split. The organic layer was then washed with 5 volumes of DI water until the pH of the aqueous layer was neutral. The organic layer (DCM) is filtered through a medium fritted glass filter prior to proceeding with the solvent exchange.

An atmospheric distillation was performed in order to reduce the volume of DCM to a level of 3.75× (150 mL). At this point, IPA (3.75×; 150 mL) was introduced into the flask and the atmospheric distillation was resumed until the volume of the batch reached once again 3.75× (150 mL). An additional 3.75× (150 mL) IPA was introduced to the flask and distillation was continued until the final volume of the batch was 3.75× (150 mL). The batch temperature during this stage was equivalent to the boiling point of IPA (~82° C.). To the hot solution (75±5° C.) of product in IPA was added water (3×; 120 mL) at such a rate that the temperature is maintained above 70° C. The mixture was cooled to 5° C. over a >1 hour period and held for 75 minutes. The solids were filtered, and washed with a minimum amount (~2×) of cold (5° C.) IPA/water mixture (40/60). The solid was dried in a vacuum oven at 55° C. for 17 hours. Isolated 27.97 g of product (19) (95.1% uncorrected yield; 99.76% de).

Example 8

Preparation of (5S)-2-(bicyclo[2.2.1]hept-5-en-2-ylamino)-5-isopropyl-5-methylthiazol-4(5H)-one (23) of high diastereomeric excess Step 1

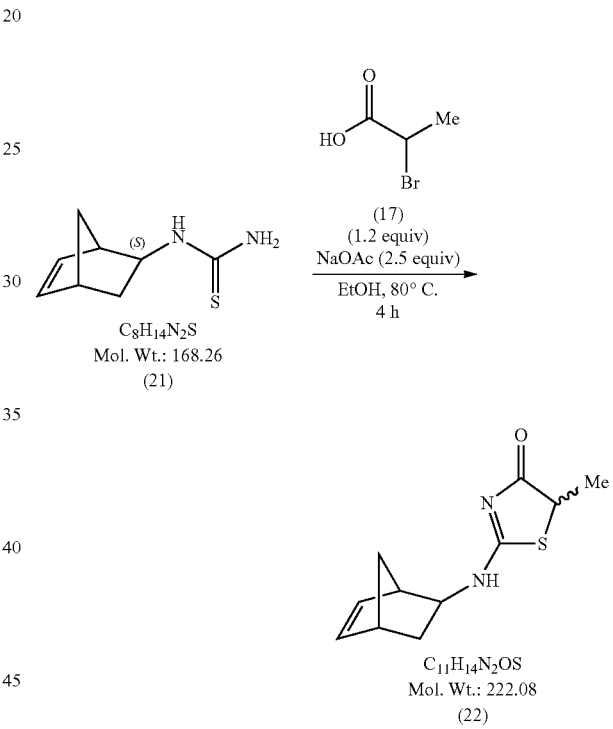

A 20 L reactor was placed under a nitrogen sweep. (S)-exo-2-norbornenylthiourea (21) (587 g) was charged to the reactor followed by 2.97 L of absolute ethanol. Agitation was initiated, and this was followed by addition of 2-bromopropionic acid (17) (377 mL) via a graduated cylinder. Sodium acetate (715 g) was then charged. The reaction mixture was heated to 80° C. and aged at this temperature for 4 hours, after which it was cooled to 22° C. Deionized water (9 L) was added and a small exotherm resulted. The mixture was allowed to return to 22° C. and aged for 12 h. The resulting suspension was filtered through a medium-porosity sintered glass funnel. The solid remaining in the reactor was rinsed into the funnel with deionized water (1.5 L) and the filter cake was washed with 0.5 L of deionized water. The solid was air-dried on the filter for 3 hours, then transferred to drying trays and dried at 50° C. and 3-30 ton until TGA analysis indicated water content of less than 3.0%. The dry weight was recorded (728.9 g, 94% yield).

Step 2: Asymmetric alkylation

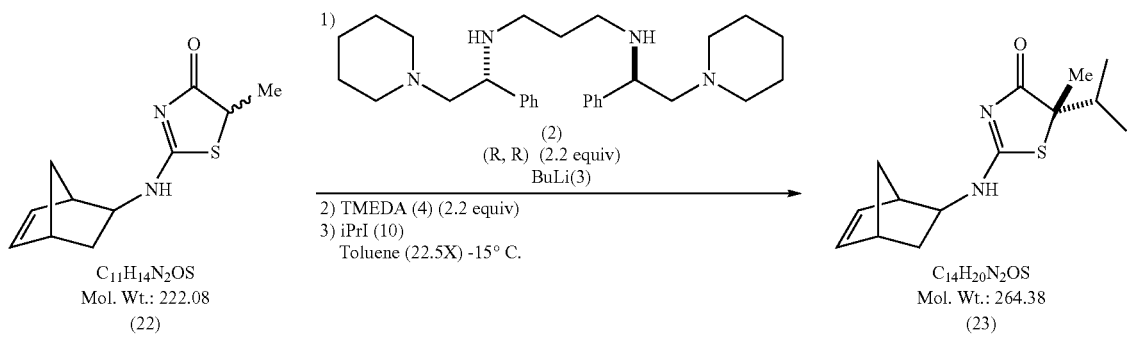

A 20 L reactor was placed under a nitrogen sweep as stated. (R,R)-chiral amine (2) amine (1610 g) was charged to the reactor. This was followed by a nitrogen sweep for 50 minutes. Anhydrous toluene (5.42 L) was then charged and agitation was initiated. The reaction mixture was allowed to stir under a nitrogen sweep for an additional 10 minutes, after which the reaction mixture was cooled to −7.5° C. over 45 minutes. The dropping funnel was charged with n-BuLi (3) solution (2.66 L), and dropwise addition of the n-BuLi was initiated. During this addition, the addition rate and jacket temperature were adjusted to ensure that internal temperature did not rise above 0° C. Once the addition was complete, the dropping funnel was rinsed with anhydrous toluene (100 mL) transferred via cannula from a sure-seal bottle of toluene. The reaction mixture was cooled to −15° C., and TMEDA (4) (540 mL) was then added via cannula. 5-methylthiazolinone (22) (361.6 g) was slurried in anhydrous toluene (1.45 L) in a separate 5 L, 3-neck round-bottom flask under a nitrogen sweep for 30 minutes. The resulting shiny was charged portion wise to the reactor via cannula, adjusting addition rate and jacket temperature so as to maintain the internal temperature below 0° C. The round-bottom flask used to prepare the substrate slurry was rinsed with toluene (2×468 mL) and the washes were charged to the reactor The reaction mixture was warmed to 15° C. over 1.5 hours, and aged at this temperature for 30 min (with chiller set at 22° C., max temp=20° C.). The mixture was then re-cooled to −15° C. over one hour. 2-Iodopropane (10) (1.3 L) was charged via cannula at such a rate as to maintain temperature below −12.5° C., adjusting the jacket temperature as needed to control the resulting exotherm.

The reaction mixture was allowed to age at −15° C. until >93% conversion was obtained, and then quenched by dropwise addition of saturated NH$_4$Cl solution (3.62 L), again adjusting addition rate and jacket temperature to control the resulting exotherm. The reaction mixture was warmed to room temperature and agitation was halted. Phases were allowed to separate and the lower aqueous layer was drained. 4.82 L of saturated NH$_4$Cl solution was added and the mixture agitated for 20 minutes. The phases were allowed to separate and the lower aqueous layer was drained. Acetic acid solution (2 M, 3 L) was charged to the reactor, and the mixture agitated for 30 minutes. The phases were allowed to separate and the lower aqueous layer was drained. This acetic acid wash was repeated. Saturated NaHCO$_3$ solution (3 L) was charged to the reactor slowly while agitating for 20 minutes. The phases were allowed to separate (at least 20 min). The lower aqueous phase was drained. Water (3 L) was charged to the reactor slowly while agitating for 20 minutes. The phases were allowed to separate and the lower aqueous phase was drained.

The toluene layer was solvent-swapped into octane, with the final ratio of solvents ~20:1, octane:toluene. The distillation was performed with the internal temperature within the range of 19° C.-54° C., and the pressure within the range of 40-275 torr. After the desired solvent ratio was reached, with a final volume of 3.9 L, the slurry was filtered through a medium-porosity sintered glass funnel, rinsing with two portions of octane (1400 mL total). The solids were dried on the filter for 1-1.5 hours, and then transferred to a drying dish and dried in a vacuum oven at 45-55° C., 3-30 ton for 18-42 hours. Obtained 370 g of a white solid, 86% yield, 80.5% de.

Step 3 (MSA Salting)

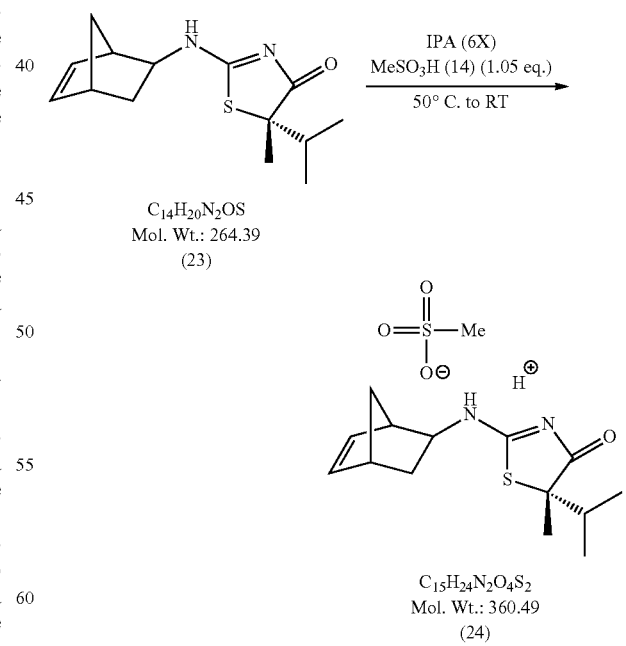

A 5 L reactor was placed under a N$_2$ (g) atmosphere. Alkylation product (23) (80.5% de; 303.3 g) was then charged, followed by isopropyl alcohol (1820 mL, 6 volumes). Agitation was established and methanesulfonic acid

(14) (78.2 mL) was then charged via addition funnel. The reaction mixture was heated to 50° C. and aged for 1 hour. The reactor contents were then cooled to 20-24° C. and aged for 1.5 hours. The solid was then isolated by filtration through a 2 L medium-porosity sintered glass funnel. Two additional portions of isopropyl alcohol (2×303 mL, 2 volumes total) were used to rinse any remaining solid material from the 5 L reactor. The wetcake was allowed to dry on the funnel for at least 1 hour. The solid material was then transferred to a drying tray and placed in a vacuum oven at 50° C., 3-30 ton for 16 hours. Obtained 367.4 g (88.9% uncorrected yield, 96.8% de) of dry compound.

The isolated solid (367.4 g) was recharged to the reactor followed by isopropyl alcohol (1886 mL). Agitation was established and the reactor contents were heated to 50° C. over 105 minutes. The mixture was aged at this temperature for 23 hours. It was then cooled to 20-24° C. over 2 hours and aged for an additional 3 hours. The solid was isolated by filtration through an 8 L medium-porosity sintered glass funnel. An additional portion of isopropyl alcohol (2×269 mL) was used to rinse the wet cake. The solid material was allowed to dry on the funnel for at least 1 hour. It was then transferred to a drying tray and placed in a vacuum oven at 50° C. for 16 hours. Obtained 357.2 g (97.2% yield, 99.3% de) of dry compound.

Step 4 (Free Basing)

returned to the reactor for water washes. The reactor was charged with 2.86 L of DI water and the biphasic mixture was stirred for 15 minutes. Agitation was then stopped and the layers were allowed to settle. The lower organic layer was drained. The upper aqueous layer was then drained (pH=10). The water wash was repeated once, resulting in a pH of 7. The final organic layer was filtered through a medium porosity sintered glass funnel and returned to a clean 20 L reactor equipped with a distillation apparatus.

A vacuum distillation was performed in order to reduce the volume from 7.8 L to 4.0 L (6.7×). The range in temperature was 11° C. to 40° C., and the range in pressure was 80-180 torr. When a volume of 4.0 L was reached, 4.0 L of IPA was added and the vacuum distillation repeated until a volume of 3.0 L (6.8 volumes) was reached, and DCM levels were undetectable. At this point, the solution was warmed to 60° C. over 2 hours, and then 2420 L of DI water were added over 10 minutes, resulting in an 8° C. temperature decrease. The chiller was then ramped to 35° C., and when the internal temperature reached 41° C., an additional 580 mL DI water was added (total water=6.8 volumes, IPA: Water=1:1). Over one hour the temperature of the solution was ramped down to 0° C.-3° C., and then the solution was filtered through a 8 L M porosity sintered glass funnel. The solids were rinsed with 880 mL (2×) of a 70:30 water:IPA mixture. The resulting material was transferred to a drying tray and placed in a vacuum oven at 50° C., 3-30 torr for 16 hours. Obtained 392.3 g (89.3% yield, 99.3% de) of a white solid (23).

Example 9

Preparation of lithium (R)-propane-1,3-diylbis(((R)-1-phenyl-2-(piperidin-1-yl)ethyl)amide) (25)

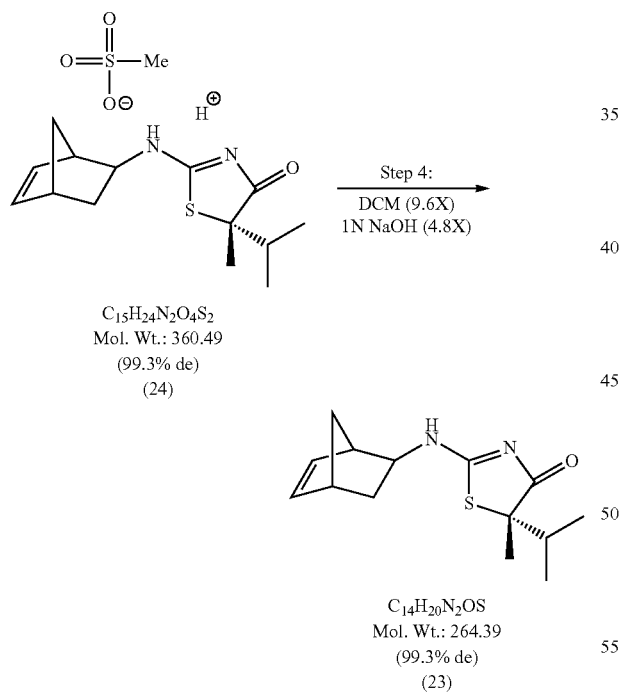

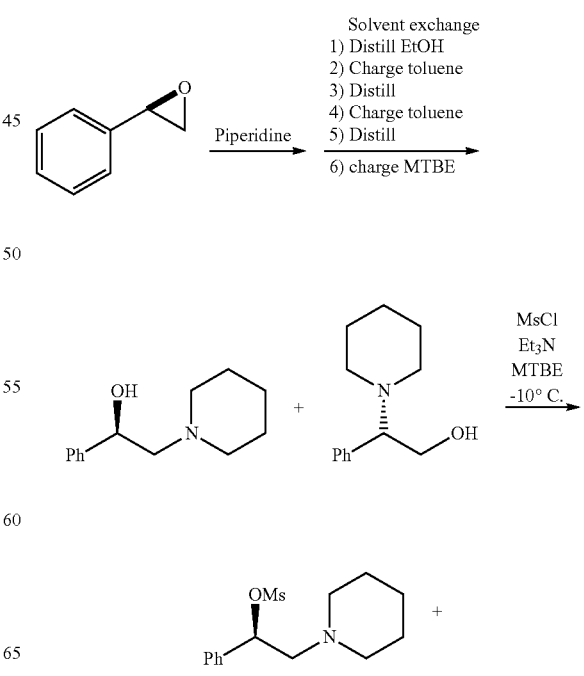

A 20 L reactor was placed under a nitrogen sweep. The reactor was charged with methanesulfonic acid salt (24) (598.6 g), and 5.73 L of dichloromethane. Agitation was initiated and 2.86 L of 1N sodium hydroxide was added to the suspension over 10 minutes, which caused a rise in temperature from 18.1° C. to 21.6° C. This mixture was agitated for one hour then stopped, and the layers were allowed to settle. The lower organic layer was drained. The upper aqueous layer was then drained (pH=14). The organic layer was -continued

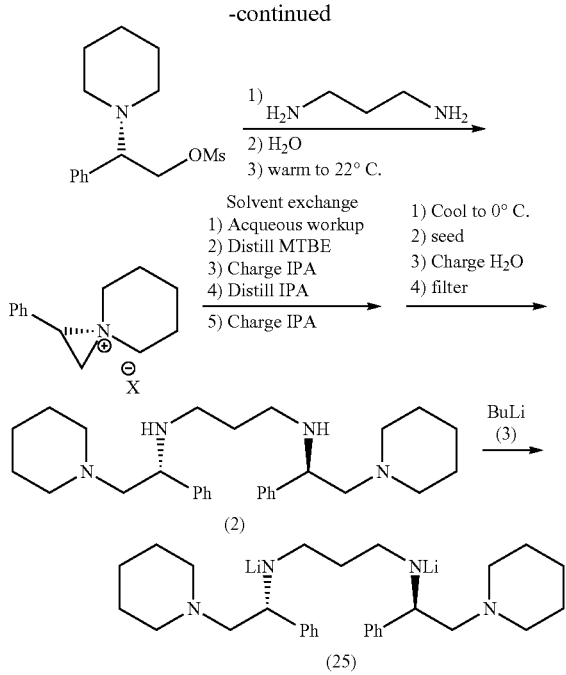

Other chiral bases described herein may be prepared readily by procedures that are analogous to the method shown in scheme above.

Example 10

One-pot Alkylation Reaction to Make (5S)-2-(bicyclo[2.2.1]heptan-2-ylamino)-5-isopropyl-5-methylthiazol-4(5H)-one A 3-neck 250 mL round-bottom flask equipped with an overhead stirrer and thermocouple was charged with 5-methylthiazolinone (2 g, 8.92 mmol, 1 equiv)

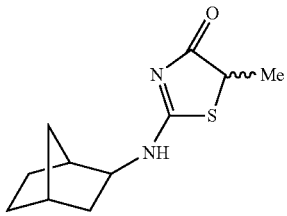 [SMILES: CC1SC(NC2CC3CCC2C3)=NC1=O]

and amine (8.8 g, 19.6 mmol, 2.2 equiv)

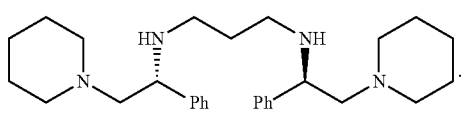 [SMILES: c1ccc([C@H](CN2CCCCC2)NCCCN[C@@H](CN2CCCCC2)c2ccccc2)cc1]

One neck was capped with a septum, and a needle inserted which was connected to a nitrogen and vacuum source. The flask was evacuated and back-filled with nitrogen. Toluene (40 mL, 20 volumes, Aldrich Sure-Seal) was charged via syringe to the flask. Agitation was initiated, and a needle was inserted in the septum under a positive pressure of nitrogen to purge the atmosphere. TMEDA (2.96 mL, 19.6 mmol, 2.2 equiv) was added via syringe, and the atmosphere was purged for 5 min. The solution was cooled to −15° C. (+/−5° C.), and the n-BuLi (2.6 M in toluene) (15.1 mL, 39.2 mmol, 4.4 equiv) was added via syringe over 35 minutes. The temperature did not exceed −15° C. (+/−5° C.). The reaction pot was warmed to 22° C. (+/−3° C.) over 30 min and then held for 90 min. At this point, the reaction was cooled to 0° C. (+/−3° C.) and 2-iodopropane (7.14 mL, 71.4 mmol, 8.0 equiv) was added over 15 min. A small latent exotherm of ~4° C. was observed. The reaction was allowed to warm to 22° C. over 1-2 h, and then held at 22° C. for an additional 16 h. The reaction was quenched with saturated aqueous ammonium chloride (16 mL, 8 volumes) by adding it drop-wise via syringe over 30 min. The reaction mixture was added to a separatory funnel, and the two layers were separated. The upper organics layer was found to contain 1.86 g, 78% assay yield (uncorrected) of (5S)-2-(bicyclo[2.2.1]heptan-2-ylamino)-5-isopropyl-5-methylthiazol-4(5H)-one with a stereo selectivity of 87:13 and 110 mg, 5.5% of starting material. This reaction stream can be worked-up in the same manner as a two-pot alkylation reaction.

Example 11

One-Pot Asymmetric Alkylation Using (+)-Ephedrine HCl

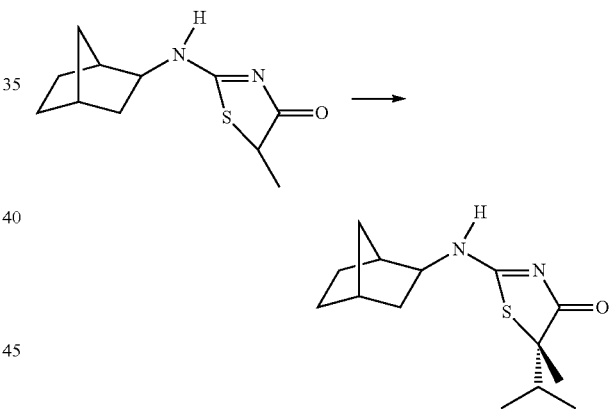

A. Using 2.5 M n-Butyllithium in Hexanes

A 5 L reactor equipped with an overhead stirrer and a 5-port lid which was connected to an addition funnel, a nitrogen inlet, and a thermocouple was charged with 5-methylthiazolinone (95.5 g, 0.426 mol, 1.0 equiv)

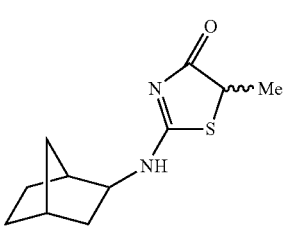 [SMILES: CC1SC(NC2CC3CCC2C3)=NC1=O]

and (1S,2R)-(+)-ephedrine HCl (103.1 g, 0.511 mol, 1.2 equiv)

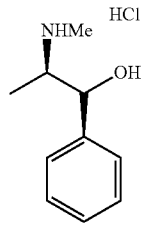

The reactor was purged with nitrogen for 45 min. by blowing nitrogen into the inlet adapter and then out through an attached outlet adapter. Me-THF (573 mL, 493 g, 6 volumes) was added via cannula, and the reactor was purged for an additional 30 min. The nitrogen outlet adapter was removed so that the reactor was under a blanket of nitrogen, and then the reactor was cooled to −15° C. (+/−3° C.). 2.5 M n-butyllithium in hexanes (0.815 L, 2.04 mol, 4.8 equiv) was charged to an addition funnel via cannula. The chiller attached to the reactor was set to −30° C., and the butyllithium was added to the reactor drop-wise over 2 h such that the internal temperature did not exceed −9° C. After the addition was complete, the reactor was warmed to 22° C. (+/−3° C.) over 1 h and held at this temperature for 30 min. At this point, the addition of 2-iodopropane (341 mL, 3.41 mol, 8.0 equiv) portion-wise from an inert round-bottom flask was begun. 10 minutes into the addition, the chiller was set to 10° C. in order to absorb a small exotherm which brought the temperature to 26° C. The entire addition took 25 min., and the chiller was re-set to 22° C. This reaction mixture stirred at 22° C. for 16 h, and analysis of an aliquot by HPLC revealed >99% conversion and 77:23 dr. The chiller was set to 10° C., and sulfuric acid (1.05 M, 907 mL, 9.5 volumes) was added drop-wise via an addition funnel over 45 min. The chiller was re-set to 22° C., and this mixture was stirred for 1 h. Dichloromethane (478 mL, 5 volumes) and water (287 mL, 3 volumes) were added and stirred 10 min. After separation, the lower aqueous layer (1.4 Kg) was drained, analyzed by HPLC, and found to contain 45 g of ephedrine (53%). Sodium bisulfate monohydrate (20 w/v %, 907 mL, 9.5 volumes) was added to the reactor and the two layers were agitated for 30 min. The lower aqueous layer (1 Kg) was drained, analyzed by HPLC, and found to contain 19 g (23%) of ephedrine.

The organics, (2.2 Kg) were drained, analyzed by HPLC, and found to contain the desired (5S)-2-(bicyclo[2.2.1]heptan-2-ylamino)-5-isopropyl-5-methylthiazol-4(5H)-one (101 g, 89%, 77:23 dr) and (+)-ephedrine (2.9 g, 3%). An additional sodium bisulfate monohydrate (20 w/v %, 907 mL, 9.5 volumes) wash can be incorporated here, if needed, to remove excess ephedrine. The organics were returned to the reactor and washed with sodium bicarbonate (sat. aq.) (907 mL, 9.5 volumes), the layers drained, and the organics subjected to salting and freebasing in a manner analogous to steps 3 and 4 of Example 7 above to isolate the product.

B. Using 6.6 M n-Hexyllithium in Hexanes

A 100 mL round-bottom flask equipped with a thermocouple was charged with 5-methylthiazolinone (5 g, 22.3 mmol, 1.0 equiv)

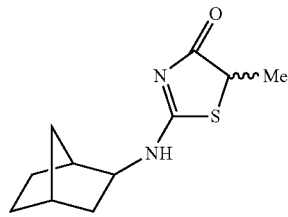

and (1S,2R)-(+)-ephedrine HCl (5.4 g, 26.7 mmol, 1.2 equiv). A septum was added to seal the flask, and it was then evacuated and backfilled with nitrogen (g). Me-THF (30 mL, 6 volumes) was added via syringe, and the flask was cooled to −15° C. (+/−3° C.). n-hexyllithium in hexanes (6.6 M, 16.2 mL, 107 mmol, 4.8 equiv) was added drop-wise to the flask via syringe over 20 min. so that the internal temperature did not exceed −15° C. (+/−3° C.). The flask was warmed to 22° C. (+/−3° C.) over 30 minutes and held at that temperature for 45 min. 2-iodopropane (17.8 mL, 178 mmol, 8.0 equiv) was added to the flask at 22° C. (+/−3° C.) over 5 min., and a small latent exotherm to 26° C. was observed. This reaction mixture stirred at 22° C. (+1-3° C.) for 16 h, and then sulfuric acid (1.05 M, 47 mL, 9.5 volumes) was added drop-wise to the reaction mixture over 90 min. The internal temperature did not exceed 26° C. during this addition. Dichloromethane (15 mL, 3 volumes) and water (10 mL, 2 volumes) were added to the reaction mixture and stirred to dissolve precipitate. The layers were transferred to a separatory funnel and the lower aqueous layer (70 g) was drained, analyzed by HPLC, and found to contain ephedrine (3.5 g, 80%). The organic layer was washed with sodium bisulfate monohydrate (20 w/v %, 47 mL, 9.5 volumes) and the layers were allowed to separate. The lower aqueous layer (56 g) was drained, analyzed by HPLC, and found to contain ephedrine (800 mg, 18%) and (5S)-2-(bicyclo[2.2.1]heptan-2-ylamino)-5-isopropyl-5-methylthiazol-4(5H)-one and its racemate (28 mg, 0.5%).

The organic layer (89 g) was drained, analyzed by HPLC, and found to contain (5S)-2-(bicyclo[2.2.1]heptan-2-ylamino)-5-isopropyl-5-methylthiazol-4(5H)-one (5.1 g, 85%, 76:24 dr). An additional sodium bisulfate monohydrate (20 w/v %, 47 mL, 9.5 volumes) wash can be incorporated here, if needed, to remove excess ephedrine. The organics were returned to the separatory funnel and washed with sodium bicarbonate (sat. aq.) (47 mL, 9.5 volumes). The two layers were slow to separate, and additional brine (3 volumes) was added to aid the separation. Finally, the layers separated and were drained.

We claim:

1. A process for the preparation of a compound of formula I, or a tautomer, stereoisomer, optical isomer, prodrug, or pharmaceutically acceptable salt thereof:

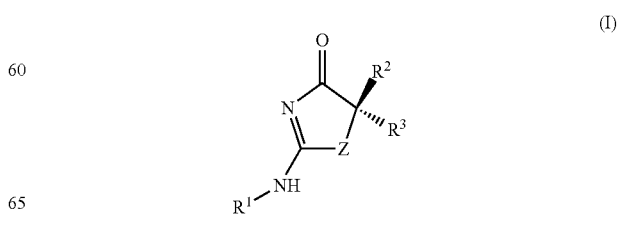

comprising
(a) contacting a compound of formula II

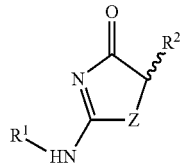
(II)

with a chiral base selected from the group consisting of:

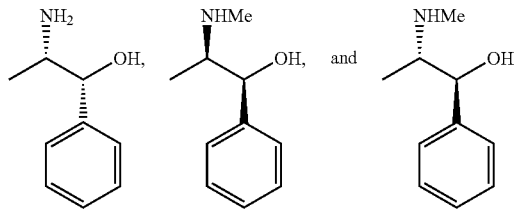

in the presence of a deprotonating reagent and alkylating agent R³-LG;
wherein:
Z is S or O;
R¹ is selected from $C_{1-8}$ alkyl, $C_{2-8}$ alkenyl, $C_{3-10}$-cycloalkyl, $C_{3-10}$-cycloalkenyl, $C_{3-10}$-cycloalkyl-$C_{1-8}$-alkyl, $C_{3-10}$-cycloalkenyl-$C_{1-8}$-alkyl, aryl, aryl-$C_{1-8}$-alkyl, heterocyclyl, heterocyclyl-$C_{1-8}$-alkyl and haloalkyl;
wherein any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^4R^5N$—$C_1$-$C_8$-alkyl, $C_1$-$C_8$-alkyl-$OR^6$, —$OR^6$, $(C_3$-$C_{10})$-cycloalkyl or $C_1$-$C_8$-alkyl-sulfonyl;
R² and R³ are independently selected from $C_{1-8}$-alkyl, $C_{1-8}$-alkoxy, $C_{3-10}$-cycloalkyl, heterocyclyl, $C_{3-10}$-cycloalkyl-$C_{1-8}$-alkyl, CN—$C_{1-8}$-alkyl, aryl, aryl-$C_{1-8}$-alkyl, heterocyclyl-$C_{1-8}$-alkyl and haloalkyl;
wherein any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^4R^5N$—$C_1$-$C_8$-alkyl, $C_1$-$C_8$-alkyl-$OR^6$, —$OR^6$, $(C_3$-$C_{10})$-cycloalkyl or $C_1$-$C_8$-alkyl-sulfonyl;
R⁴ and R⁵ are each independently selected from hydrogen, $C_1$-$C_8$ alkyl, $C_1$-$C_8$ alkoxy, —$NR^6R^6$, —S—$(C_1$-$C_8)$ alkyl, aryl and heterocyclyl;
where in the definition of R⁴ and R⁵ any alkyl, alkoxy, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$) alkyl
R⁶ is independently selected from hydrogen, $C_1$-$C_8$ alkyl, aryl-$C_1$-$C_8$ alkyl, $C_1$-$C_8$ alkoxy, —S—$(C_1$-$C_8)$alkyl, heterocyclyl and aryl;
where in the definition of R⁶ any alkyl, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl
LG is a leaving group.

2. The process according to claim 1, further comprising the steps of
(b) contacting the product of (a) with an acid HB to form a salt of formula I'

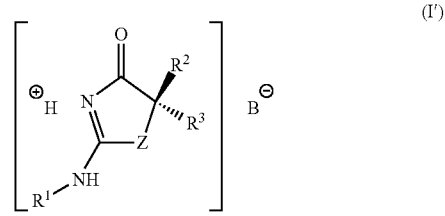
(I')

wherein B is an organic or inorganic anion; and
(c) reacting the salt of formula I' with a base to form the compound of formula I.
3. The process according to claim 1, wherein Z is S.
4. The process according to claim 1, wherein $R_1$ is selected from the group consisting of

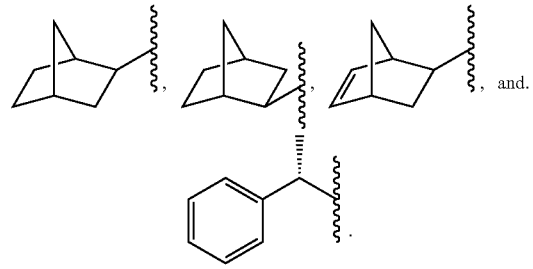

5. The process according to claim 4, wherein $R_1$ is

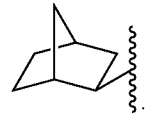

6. The process according to claim 1, wherein $R_2$ and $R_3$ are independently selected from methyl, isopropyl, and propyl.
7. The process according to claim 6, wherein $R_2$ is methyl and $R_3$ is isopropyl.
8. The process according to claim 7, wherein the chiral base is

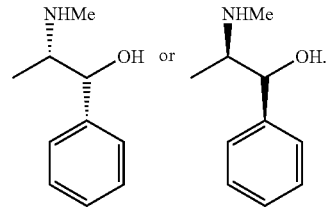

9. The process according to claim 1, wherein the de of the compound of formula I is at least 85%.
10. The process according to claim 1, wherein the leaving group LG is selected from the group consisting of Cl, Br, I, —$OS(O)_2CH_3$, —$OS(O)_2C_4F_9$, —$OS(O)_2CF_3$, and —$OS(O)_2(4$-$CH_3$-phenyl)$.

11. A process for the preparation of a compound according to formula III:

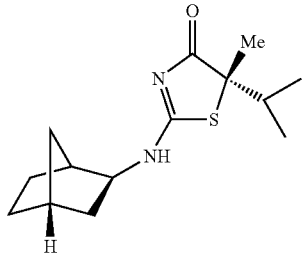

(III)

comprising
(a) contacting a compound of formula (IV)

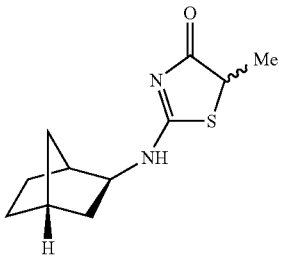

(IV)

with a chiral base selected from the group consisting of:

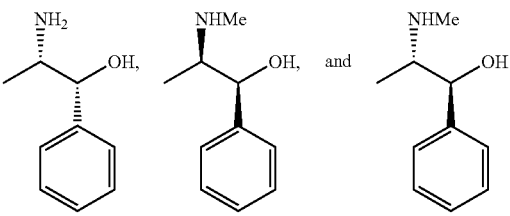

or an acid addition salt thereof in the presence of a deprotonating reagent and;
(b) reacting the product of step (a) with isopropyl iodide.

12. The process according to claim 11, wherein the chiral base is

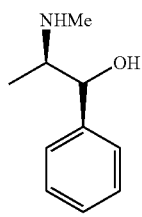

or an acid addition salt thereof.

* * * * *